(12) United States Patent
Hunt et al.

(10) Patent No.: US 12,186,165 B2
(45) Date of Patent: Jan. 7, 2025

(54) OPTICAL FIBERS FOR OPTICALLY SENSING THROUGH WOUND DRESSINGS

(71) Applicant: T.J.Smith and Nephew, Limited, Hull (GB)

(72) Inventors: Allan Kenneth Frazer Grugeon Hunt, Beverley (GB); Lee Ian Partington, Hessle (GB); Marcus Damian Phillips, Wakefield (GB); Felix Clarence Quintanar, Hull (GB)

(73) Assignee: T.J.Smith and Nephew, Limited, Hull (GB)

( * ) Notice: Subject to any disclaimer, the term of this patent is extended or adjusted under 35 U.S.C. 154(b) by 319 days.

(21) Appl. No.: 17/280,109

(22) PCT Filed: Sep. 26, 2019

(86) PCT No.: PCT/EP2019/076049
§ 371 (c)(1),
(2) Date: Mar. 25, 2021

(87) PCT Pub. No.: WO2020/064937
PCT Pub. Date: Apr. 2, 2020

(65) Prior Publication Data
US 2021/0338489 A1    Nov. 4, 2021

(30) Foreign Application Priority Data
Sep. 28, 2018  (GB) ........................ 1815854

(51) Int. Cl.
*A61F 13/05*   (2024.01)
*A61L 15/22*   (2006.01)
*A61M 1/00*    (2006.01)

(52) U.S. Cl.
CPC .............. *A61F 13/05* (2024.01); *A61L 15/22* (2013.01); *A61M 1/90* (2021.05); *A61M 2205/3331* (2013.01); *A61M 2205/3368* (2013.01)

(58) Field of Classification Search
CPC .......... A61F 13/0216; A61F 2013/0094; A61F 2013/00953; A61F 2013/00957;
(Continued)

(56) References Cited

U.S. PATENT DOCUMENTS

| | | |
|---|---|---|
| 3,896,802 A | 7/1975 | Williams |
| 4,334,530 A | 6/1982 | Hassell |

(Continued)

FOREIGN PATENT DOCUMENTS

| | | |
|---|---|---|
| CN | 105232229 A | 1/2016 |
| CN | 105395184 A | 3/2016 |

(Continued)

OTHER PUBLICATIONS

Aubakir B., et al., "Vital Sign Monitoring Utilizing Eulerian Video Magnification and Thermography," 38th Annual International Conference of the IEEE Engineering in Medicine and Biology Society, Aug. 16, 2016, pp. 3527-3530 (4 pages).

(Continued)

*Primary Examiner* — Susan S Su
*Assistant Examiner* — Katherine-Ph Minh Pham
(74) *Attorney, Agent, or Firm* — Knobbe, Martens, Olson & Bear, LLP

(57) ABSTRACT

A wound treatment apparatus can include a wound dressing configured to be positioned proximate to a wound. Multiple optical fibers positioned at least partly in the wound dressing can include a first optical fiber and a second optical fiber. The wound treatment apparatus can include an emitter and a detector. The emitter can emit first electromagnetic radia- (Continued)

tion into the first optical fiber so that the first optical fiber passes the first electromagnetic radiation. The detector can generate a signal responsive to second electromagnetic radiation that exits the second optical fiber and contacts the detector.

20 Claims, 11 Drawing Sheets

(58) Field of Classification Search
CPC . A61L 15/22; A61M 1/90; A61M 2205/3331; A61M 2205/3368; A61M 1/95; A61M 1/966
See application file for complete search history.

(56) References Cited

U.S. PATENT DOCUMENTS

| | | |
|---|---|---|
| 5,090,410 A | 2/1992 | Saper et al. |
| 5,253,654 A | 10/1993 | Thomas et al. |
| 5,635,201 A | 6/1997 | Fabo |
| 5,642,096 A | 6/1997 | Leyerer et al. |
| 5,678,448 A | 10/1997 | Fullen et al. |
| 5,690,610 A | 11/1997 | Ito et al. |
| 5,836,990 A | 11/1998 | Li |
| 5,917,180 A * | 6/1999 | Reimer ............... G01L 1/24 250/227.14 |
| 6,095,992 A | 8/2000 | Augustine |
| 6,178,342 B1 | 1/2001 | Borgos et al. |
| 6,381,482 B1 | 4/2002 | Jayaraman et al. |
| 6,517,484 B1 | 2/2003 | Wilk et al. |
| 6,551,252 B2 | 4/2003 | Sackner et al. |
| 6,731,987 B1 | 5/2004 | McAdams et al. |
| 7,077,832 B2 | 7/2006 | Fleischmann |
| 7,088,591 B2 | 8/2006 | Kishimoto et al. |
| 7,201,063 B2 | 4/2007 | Taylor |
| 7,206,623 B2 | 4/2007 | Blank et al. |
| 7,289,205 B2 | 10/2007 | Yaroslavsky et al. |
| 7,316,652 B2 | 1/2008 | Dalgaard et al. |
| 7,429,255 B2 | 9/2008 | Thompson |
| 7,520,875 B2 | 4/2009 | Bernabei |
| 7,521,292 B2 | 4/2009 | Rogers et al. |
| 7,625,117 B2 | 12/2009 | Haslett et al. |
| 7,687,678 B2 | 3/2010 | Jacobs |
| 7,846,141 B2 | 12/2010 | Weston |
| 7,877,866 B1 | 2/2011 | Greenberg et al. |
| 7,884,258 B2 | 2/2011 | Boehringer et al. |
| 7,904,133 B2 | 3/2011 | Gehman et al. |
| 7,922,676 B2 | 4/2011 | Daskal et al. |
| 7,942,869 B2 | 5/2011 | Houbolt et al. |
| 7,945,302 B2 | 5/2011 | McAdams |
| 8,019,401 B1 | 9/2011 | Smith et al. |
| 8,032,210 B2 | 10/2011 | Finneran et al. |
| 8,060,174 B2 | 11/2011 | Simpson et al. |
| 8,079,247 B2 | 12/2011 | Russell et al. |
| 8,111,165 B2 | 2/2012 | Ortega et al. |
| 8,116,841 B2 | 2/2012 | Bly et al. |
| 8,182,425 B2 | 5/2012 | Stamatas et al. |
| 8,238,996 B2 | 8/2012 | Burnes et al. |
| 8,241,231 B2 | 8/2012 | Bausewein et al. |
| 8,332,053 B1 | 12/2012 | Patterson et al. |
| 8,333,874 B2 | 12/2012 | Currie |
| 8,480,641 B2 | 7/2013 | Jacobs |
| 8,553,223 B2 * | 10/2013 | McKenna ............ G02B 6/02033 356/319 |
| 8,579,872 B2 | 11/2013 | Coulthard et al. |
| 8,632,523 B2 | 1/2014 | Eriksson et al. |
| 8,644,911 B1 | 2/2014 | Panasyuk et al. |
| 8,682,442 B2 | 3/2014 | McAdams |
| 8,758,237 B2 | 6/2014 | Sherman et al. |
| 8,783,948 B2 | 7/2014 | Panda et al. |
| 8,788,009 B2 | 7/2014 | Greene et al. |
| 8,800,386 B2 | 8/2014 | Taylor |
| 8,818,478 B2 | 8/2014 | Scheffler et al. |
| 8,848,187 B2 | 9/2014 | Uematsu et al. |
| 8,894,590 B2 | 11/2014 | Lamoise et al. |
| 8,925,392 B2 | 1/2015 | Esposito et al. |
| 8,934,957 B2 | 1/2015 | Dias et al. |
| 8,934,965 B2 | 1/2015 | Rogers et al. |
| 8,943,897 B2 | 2/2015 | Beauvais et al. |
| 8,948,839 B1 | 2/2015 | Longinotti-Buitoni et al. |
| 8,997,588 B2 | 4/2015 | Taylor |
| 9,000,251 B2 | 4/2015 | Murphy et al. |
| 9,042,075 B2 | 5/2015 | Borini et al. |
| 9,192,531 B2 | 11/2015 | Wu |
| 9,204,806 B2 | 12/2015 | Stivoric et al. |
| 9,220,455 B2 | 12/2015 | Sarrafzadeh et al. |
| 9,226,402 B2 | 12/2015 | Hsu |
| 9,282,897 B2 | 3/2016 | Ross, Jr. et al. |
| 9,314,175 B2 | 4/2016 | Jacofsky et al. |
| 9,320,473 B2 | 4/2016 | Shuler |
| 9,372,123 B2 | 6/2016 | Li et al. |
| 9,378,450 B1 | 6/2016 | Mei et al. |
| 9,386,947 B2 | 7/2016 | Johnson |
| 9,393,354 B2 | 7/2016 | Freedman et al. |
| 9,402,988 B2 | 8/2016 | Buchanan et al. |
| 9,408,573 B2 | 8/2016 | Welch et al. |
| 9,427,179 B2 | 8/2016 | Mestrovic et al. |
| 9,439,599 B2 | 9/2016 | Thompson et al. |
| 9,483,726 B2 | 11/2016 | Mei et al. |
| 9,494,474 B2 | 11/2016 | Servati et al. |
| 9,511,215 B2 | 12/2016 | Skiba |
| 9,516,758 B2 | 12/2016 | Arora et al. |
| 9,526,439 B2 | 12/2016 | Connelly et al. |
| 9,554,484 B2 | 1/2017 | Rogers et al. |
| 9,572,507 B2 | 2/2017 | Moore et al. |
| 9,582,072 B2 | 2/2017 | Connor |
| 9,585,620 B2 | 3/2017 | Paquet et al. |
| 9,587,991 B2 | 3/2017 | Padiy |
| 9,592,007 B2 | 3/2017 | Nuovo et al. |
| 9,603,560 B2 | 3/2017 | Monty et al. |
| 9,610,388 B2 | 4/2017 | Aceto et al. |
| 9,613,911 B2 | 4/2017 | Rogers et al. |
| 9,629,584 B2 | 4/2017 | Macia Barber et al. |
| 9,675,238 B2 | 6/2017 | Iida et al. |
| 9,687,195 B2 | 6/2017 | Sims et al. |
| 9,717,565 B2 | 8/2017 | Blair |
| 9,907,103 B2 | 2/2018 | Chen et al. |
| 10,004,643 B2 | 6/2018 | Luckemeyer et al. |
| 10,046,096 B2 | 8/2018 | Askem et al. |
| 10,080,524 B1 | 9/2018 | Xi |
| 10,086,117 B2 | 10/2018 | Locke et al. |
| 10,117,705 B2 | 11/2018 | Chernov et al. |
| 10,152,789 B2 | 12/2018 | Carnes et al. |
| 10,182,740 B2 | 1/2019 | Tonar et al. |
| 10,201,644 B2 | 2/2019 | Haggstrom et al. |
| 10,209,213 B2 | 2/2019 | Kang et al. |
| 10,285,620 B2 | 5/2019 | Jung et al. |
| 10,288,590 B2 | 5/2019 | Hammond et al. |
| 10,321,862 B2 | 6/2019 | Dalene et al. |
| 10,463,773 B2 | 11/2019 | Haggstrom et al. |
| 10,687,984 B2 | 6/2020 | Rovaniemi |
| 10,857,038 B2 | 12/2020 | Zamierowski et al. |
| 11,026,847 B2 | 6/2021 | Piotrowski et al. |
| 11,647,922 B2 | 5/2023 | Scherer |
| 2002/0016536 A1 | 2/2002 | Benni |
| 2002/0135752 A1 | 9/2002 | Sokolov et al. |
| 2003/0033032 A1 | 2/2003 | Lind et al. |
| 2003/0208148 A1 | 11/2003 | Sullivan |
| 2003/0210810 A1 | 11/2003 | Gee, Jr. et al. |
| 2003/0216630 A1 | 11/2003 | Jersey-Willuhn et al. |
| 2004/0073151 A1* | 4/2004 | Weston ............... A61M 1/982 602/41 |
| 2004/0193218 A1* | 9/2004 | Butler ............... A61M 3/022 607/1 |
| 2004/0230132 A1 | 11/2004 | Shehada |
| 2005/0088832 A1 | 4/2005 | Su et al. |
| 2005/0240107 A1 | 10/2005 | Alfano et al. |
| 2005/0280531 A1 | 12/2005 | Fadem et al. |
| 2006/0058690 A1 | 3/2006 | Bartnik et al. |
| 2006/0173253 A1* | 8/2006 | Ganapathy ............ A61M 1/95 607/88 |
| 2006/0181791 A1 | 8/2006 | Van Beek et al. |
| 2006/0234383 A1 | 10/2006 | Gough |

(56) References Cited

U.S. PATENT DOCUMENTS

| | | |
|---|---|---|
| 2006/0241495 A1 | 10/2006 | Kurtz |
| 2007/0055209 A1 | 3/2007 | Patel et al. |
| 2007/0173892 A1 | 7/2007 | Fleischer et al. |
| 2007/0191754 A1 | 8/2007 | Aali |
| 2007/0260421 A1 | 11/2007 | Berner, Jr. et al. |
| 2007/0293748 A1 | 12/2007 | Engvall et al. |
| 2008/0081973 A1 | 4/2008 | Hoarau |
| 2008/0167535 A1 | 7/2008 | Stivoric et al. |
| 2008/0258717 A1 | 10/2008 | Igney et al. |
| 2008/0287747 A1 | 11/2008 | Mestrovic et al. |
| 2008/0319282 A1 | 12/2008 | Tran |
| 2008/0319283 A1 | 12/2008 | Cotton et al. |
| 2009/0149800 A1 | 6/2009 | Durand |
| 2009/0177051 A1 | 7/2009 | Arons et al. |
| 2009/0177110 A1 | 7/2009 | Lyden et al. |
| 2009/0209830 A1 | 8/2009 | Nagle et al. |
| 2009/0209896 A1 | 8/2009 | Selevan |
| 2009/0234206 A1 | 9/2009 | Gaspard et al. |
| 2009/0245601 A1 | 10/2009 | Cohen et al. |
| 2010/0022990 A1 | 1/2010 | Karpowicz et al. |
| 2010/0025831 A1 | 2/2010 | Yamazaki et al. |
| 2010/0166252 A1 | 7/2010 | Ahmed et al. |
| 2010/0168727 A1 | 7/2010 | Hancock et al. |
| 2010/0268111 A1 | 10/2010 | Drinan et al. |
| 2010/0305473 A1 | 12/2010 | Yuzhakov |
| 2011/0004088 A1 | 1/2011 | Grossman |
| 2011/0015591 A1 | 1/2011 | Hanson et al. |
| 2011/0054283 A1 | 3/2011 | Shuler |
| 2011/0130697 A1 | 6/2011 | Nagle et al. |
| 2011/0140703 A1 | 6/2011 | Chiao et al. |
| 2011/0190639 A1 | 8/2011 | Peltie et al. |
| 2011/0213319 A1* | 9/2011 | Blott ............... A61F 13/00063 604/291 |
| 2011/0218757 A1 | 9/2011 | Callsen et al. |
| 2011/0242532 A1 | 10/2011 | McKenna |
| 2011/0245682 A1 | 10/2011 | Robinson et al. |
| 2011/0301441 A1 | 12/2011 | Bandic et al. |
| 2012/0029306 A1 | 2/2012 | Paquet et al. |
| 2012/0029307 A1 | 2/2012 | Paquet et al. |
| 2012/0029410 A1 | 2/2012 | Koenig et al. |
| 2012/0112347 A1 | 5/2012 | Eckhardt et al. |
| 2012/0165717 A1 | 6/2012 | Al Khaburi |
| 2012/0190956 A1 | 7/2012 | Connolly |
| 2012/0190989 A1 | 7/2012 | Kaiser et al. |
| 2012/0265120 A1 | 10/2012 | Beisang, III et al. |
| 2012/0271265 A1 | 10/2012 | Langdon |
| 2012/0277559 A1 | 11/2012 | Kohl-Bareis et al. |
| 2012/0316538 A1 | 12/2012 | Heiser et al. |
| 2012/0330252 A1 | 12/2012 | Stokes et al. |
| 2013/0041235 A1 | 2/2013 | Rogers et al. |
| 2013/0064772 A1 | 3/2013 | Swiss et al. |
| 2013/0121544 A1 | 5/2013 | Sarrafzadeh et al. |
| 2013/0123722 A1 | 5/2013 | Pratt et al. |
| 2013/0151223 A1 | 6/2013 | Zamierowski et al. |
| 2013/0200268 A1 | 8/2013 | Rafferty et al. |
| 2013/0261409 A1 | 10/2013 | Pathak et al. |
| 2013/0271278 A1 | 10/2013 | Duesterhoft et al. |
| 2013/0274563 A1 | 10/2013 | Duesterhoft et al. |
| 2013/0274629 A1 | 10/2013 | Duesterhoft et al. |
| 2013/0317367 A1 | 11/2013 | Shuler |
| 2014/0012108 A1 | 1/2014 | McPeak |
| 2014/0018637 A1 | 1/2014 | Bennett et al. |
| 2014/0024905 A1 | 1/2014 | Sarrafzadeh et al. |
| 2014/0031663 A1 | 1/2014 | Gallego et al. |
| 2014/0072190 A1 | 3/2014 | Wu et al. |
| 2014/0075658 A1 | 3/2014 | McGUIN |
| 2014/0107495 A1 | 4/2014 | Marinelli et al. |
| 2014/0107498 A1 | 4/2014 | Bower et al. |
| 2014/0147611 A1 | 5/2014 | Ackerman, Jr. |
| 2014/0203797 A1 | 7/2014 | Stivoric et al. |
| 2014/0206947 A1 | 7/2014 | Isserow et al. |
| 2014/0232516 A1 | 8/2014 | Stivoric et al. |
| 2014/0235166 A1 | 8/2014 | Molettiere et al. |
| 2014/0243709 A1 | 8/2014 | Gibson et al. |
| 2014/0296749 A1 | 10/2014 | Reid, Jr. et al. |
| 2014/0298927 A1 | 10/2014 | Allin et al. |
| 2014/0298928 A1 | 10/2014 | Duesterhoft et al. |
| 2014/0303463 A1 | 10/2014 | Robinson et al. |
| 2014/0324120 A1 | 10/2014 | Bogie et al. |
| 2014/0340857 A1 | 11/2014 | Hsu et al. |
| 2014/0343478 A1 | 11/2014 | Brennan et al. |
| 2014/0350882 A1 | 11/2014 | Everett et al. |
| 2015/0018792 A1 | 1/2015 | Marsiquet et al. |
| 2015/0025343 A1 | 1/2015 | Gareau et al. |
| 2015/0138330 A1 | 5/2015 | Krishnamoorthi |
| 2015/0141767 A1 | 5/2015 | Rogers et al. |
| 2015/0148760 A1 | 5/2015 | Dodd et al. |
| 2015/0150479 A1 | 6/2015 | Yoshino et al. |
| 2015/0182166 A1 | 7/2015 | Evans et al. |
| 2015/0223716 A1 | 8/2015 | Korkala et al. |
| 2015/0257644 A1 | 9/2015 | Cao |
| 2015/0265191 A1 | 9/2015 | Harding et al. |
| 2015/0292968 A1 | 10/2015 | Vogt et al. |
| 2015/0313476 A1 | 11/2015 | Pisani et al. |
| 2015/0313533 A1 | 11/2015 | Rapp et al. |
| 2015/0327777 A1 | 11/2015 | Kostic et al. |
| 2015/0335254 A1 | 11/2015 | Fastert et al. |
| 2015/0335287 A1 | 11/2015 | Neuman et al. |
| 2015/0335288 A1 | 11/2015 | Toth et al. |
| 2015/0351970 A1 | 12/2015 | Dagger et al. |
| 2015/0359485 A1 | 12/2015 | Berg et al. |
| 2015/0374309 A1 | 12/2015 | Farkas et al. |
| 2016/0015962 A1 | 1/2016 | Shokoueinejad Maragheh et al. |
| 2016/0022223 A1 | 1/2016 | Grundfest et al. |
| 2016/0029900 A1 | 2/2016 | LaPlante et al. |
| 2016/0030132 A1 | 2/2016 | Cheung et al. |
| 2016/0038045 A1 | 2/2016 | Shapiro |
| 2016/0038083 A1 | 2/2016 | Ding et al. |
| 2016/0051147 A1 | 2/2016 | Cohen et al. |
| 2016/0058380 A1 | 3/2016 | Lee et al. |
| 2016/0066854 A1 | 3/2016 | Mei et al. |
| 2016/0069743 A1 | 3/2016 | McQuilkin et al. |
| 2016/0074234 A1 | 3/2016 | Abichandani et al. |
| 2016/0081580 A1 | 3/2016 | Bergelin et al. |
| 2016/0081601 A1 | 3/2016 | Ballam et al. |
| 2016/0100790 A1 | 4/2016 | Cantu et al. |
| 2016/0100987 A1 | 4/2016 | Hartwell et al. |
| 2016/0101282 A1 | 4/2016 | Bergelin et al. |
| 2016/0129469 A1 | 5/2016 | Kulinsky et al. |
| 2016/0143534 A1 | 5/2016 | Hyde et al. |
| 2016/0157779 A1 | 6/2016 | Baxi et al. |
| 2016/0165719 A1 | 6/2016 | Li et al. |
| 2016/0213269 A1 | 7/2016 | Lam et al. |
| 2016/0228049 A1 | 8/2016 | Nackaerts et al. |
| 2016/0232807 A1 | 8/2016 | Ghaffari et al. |
| 2016/0242331 A1 | 8/2016 | Park et al. |
| 2016/0249810 A1 | 9/2016 | Darty et al. |
| 2016/0262672 A1 | 9/2016 | Hammond et al. |
| 2016/0262687 A1 | 9/2016 | Vaidyanathan et al. |
| 2016/0270700 A1 | 9/2016 | Baxi et al. |
| 2016/0287177 A1 | 10/2016 | Huppert et al. |
| 2016/0302729 A1 | 10/2016 | Starr et al. |
| 2016/0310023 A1 | 10/2016 | Chachisvilis et al. |
| 2016/0317057 A1 | 11/2016 | Li et al. |
| 2016/0331263 A1 | 11/2016 | Cailler et al. |
| 2016/0331322 A1 | 11/2016 | Son et al. |
| 2016/0338591 A1 | 11/2016 | Lachenbruch et al. |
| 2016/0354001 A1 | 12/2016 | Buckley et al. |
| 2016/0367189 A1 | 12/2016 | Aimone et al. |
| 2016/0367192 A1 | 12/2016 | Iyengar et al. |
| 2016/0367406 A1 | 12/2016 | Barnett |
| 2017/0000407 A1 | 1/2017 | Saxby et al. |
| 2017/0007853 A1 | 1/2017 | Alford et al. |
| 2017/0027498 A1 | 2/2017 | Larson et al. |
| 2017/0079740 A1 | 3/2017 | Hufnagel et al. |
| 2017/0086519 A1 | 3/2017 | Vigano' et al. |
| 2017/0086709 A1 | 3/2017 | Khine et al. |
| 2017/0095208 A1 | 4/2017 | Oberleitner et al. |
| 2017/0143552 A1 | 5/2017 | Hartwell et al. |
| 2017/0146474 A1 | 5/2017 | Bedell et al. |
| 2017/0156594 A1 | 6/2017 | Stivoric et al. |
| 2017/0156621 A1 | 6/2017 | Bettinger et al. |
| 2017/0156658 A1 | 6/2017 | Maharbiz et al. |
| 2017/0164865 A1 | 6/2017 | Rafferty et al. |

(56) References Cited

U.S. PATENT DOCUMENTS

| | | |
|---|---|---|
| 2017/0164876 A1 | 6/2017 | Hyde et al. |
| 2017/0172439 A1 | 6/2017 | Zhu et al. |
| 2017/0202711 A1 | 7/2017 | Cernasov et al. |
| 2017/0224271 A1 | 8/2017 | Lachenbruch et al. |
| 2017/0231015 A1 | 8/2017 | Jang et al. |
| 2017/0258972 A1 | 9/2017 | Weston |
| 2017/0319075 A1 | 11/2017 | Homan et al. |
| 2017/0326004 A1 | 11/2017 | Long et al. |
| 2017/0367644 A1 | 12/2017 | Sharman et al. |
| 2018/0003579 A1 | 1/2018 | Esposito et al. |
| 2018/0008177 A1 | 1/2018 | Shimuta et al. |
| 2018/0055359 A1 | 3/2018 | Shamim et al. |
| 2018/0055697 A1 | 3/2018 | Mihali et al. |
| 2018/0056087 A1 | 3/2018 | Ribeiro et al. |
| 2018/0070880 A1 | 3/2018 | Trembly et al. |
| 2018/0074547 A1 | 3/2018 | Smadi et al. |
| 2018/0116877 A1 | 5/2018 | Ineichen |
| 2018/0132287 A1 | 5/2018 | Cheng et al. |
| 2018/0154052 A1* | 6/2018 | Chien .................. A61M 1/732 |
| 2018/0192514 A1 | 7/2018 | Seo |
| 2018/0200414 A1 | 7/2018 | Askem et al. |
| 2018/0206758 A1 | 7/2018 | Feldkamp et al. |
| 2018/0235484 A1 | 8/2018 | Mozdzierz |
| 2018/0296397 A1 | 10/2018 | Askem et al. |
| 2019/0001032 A1 | 1/2019 | Weston et al. |
| 2019/0021911 A1 | 1/2019 | Askem et al. |
| 2019/0060126 A1 | 2/2019 | Ribble et al. |
| 2019/0076298 A1 | 3/2019 | Quintanar et al. |
| 2019/0083025 A1 | 3/2019 | Aung et al. |
| 2019/0133812 A1 | 5/2019 | Seres et al. |
| 2019/0134280 A1 | 5/2019 | Toth |
| 2019/0159938 A1 | 5/2019 | Askem et al. |
| 2019/0175098 A1 | 6/2019 | Burns |
| 2019/0192066 A1 | 6/2019 | Schoess et al. |
| 2019/0231939 A1 | 8/2019 | Askem et al. |
| 2019/0290496 A1 | 9/2019 | Brownhill et al. |
| 2019/0374387 A1 | 12/2019 | Ribble et al. |
| 2020/0054218 A1 | 2/2020 | Xi |
| 2020/0078482 A1 | 3/2020 | Yoon et al. |
| 2020/0078499 A1 | 3/2020 | Gadde et al. |
| 2020/0100711 A1 | 4/2020 | Choudhury et al. |
| 2020/0147407 A1 | 5/2020 | Efremkin |
| 2020/0281512 A1 | 9/2020 | Grubb et al. |
| 2020/0281513 A1 | 9/2020 | Grubb et al. |
| 2020/0281529 A1 | 9/2020 | Grubb et al. |
| 2020/0289346 A1 | 9/2020 | Hansen et al. |
| 2020/0330258 A1 | 10/2020 | Hansen et al. |
| 2020/0360547 A1 | 11/2020 | Smith et al. |
| 2021/0212855 A1 | 7/2021 | Hansen et al. |
| 2022/0079814 A1 | 3/2022 | Chen et al. |

FOREIGN PATENT DOCUMENTS

| | | | |
|---|---|---|---|
| CN | 106102322 A | | 11/2016 |
| CN | 109350362 A | | 2/2019 |
| DE | 102012211015 A1 | | 1/2014 |
| DE | 102013013013 A1 | | 2/2015 |
| EP | 2454990 A2 | | 5/2012 |
| EP | 2565630 A1 | | 3/2013 |
| EP | 3231478 A1 | | 10/2017 |
| EP | 3409190 A1 | | 12/2018 |
| EP | 3499510 A1 | | 6/2019 |
| EP | 3837520 A1 | | 6/2021 |
| GB | 2316171 A | | 2/1998 |
| GB | 2563602 A | | 12/2018 |
| JP | 2009225863 A | | 10/2009 |
| KR | 20120119523 A | | 10/2012 |
| KR | 101224629 B1 | | 1/2013 |
| KR | 20140024743 A | | 3/2014 |
| KR | 20140058041 A | | 5/2014 |
| KR | 20160071044 A | | 6/2016 |
| KR | 20190105898 A | | 9/2019 |
| NL | 1027236 C2 | | 4/2006 |
| WO | WO-0021433 A1 | | 4/2000 |
| WO | WO-0043046 A2 | | 7/2000 |
| WO | WO-03067229 A1 | | 8/2003 |
| WO | WO-2006041997 A2 | | 4/2006 |
| WO | WO-2007030379 A2 | | 3/2007 |
| WO | WO-2008006150 A1 | | 1/2008 |
| WO | WO-2008010604 A1 | | 1/2008 |
| WO | WO-2009052607 A1 | | 4/2009 |
| WO | WO-2009120951 A2 | | 10/2009 |
| WO | WO-2009141777 A2 | | 11/2009 |
| WO | WO-2010020919 A1 | | 2/2010 |
| WO | WO-2010105053 A2 | | 9/2010 |
| WO | WO-2011082420 A1 | | 7/2011 |
| WO | WO-2011123848 A1 | | 10/2011 |
| WO | WO-2012141999 A1 | | 10/2012 |
| WO | WO-2013026999 A1 | | 2/2013 |
| WO | WO-2013044226 A2 | | 3/2013 |
| WO | WO-2014036577 A1 | | 3/2014 |
| WO | WO-2014116816 A1 | | 7/2014 |
| WO | WO-2015112095 A1 | | 7/2015 |
| WO | WO-2015168720 A1 | | 11/2015 |
| WO | WO-2016025438 A1 | | 2/2016 |
| WO | WO-2016030752 A1 | | 3/2016 |
| WO | WO-2016058032 A1 | | 4/2016 |
| WO | WO-2016073777 A1 | | 5/2016 |
| WO | WO-2016100218 A1 | | 6/2016 |
| WO | WO-2016110564 A1 | | 7/2016 |
| WO | WO-2016187136 A1 | | 11/2016 |
| WO | WO-2016205872 A1 | | 12/2016 |
| WO | WO-2016205881 A1 | | 12/2016 |
| WO | WO-2017021006 A1 | | 2/2017 |
| WO | WO-2017021965 A2 | | 2/2017 |
| WO | WO-2017033058 A1 | | 3/2017 |
| WO | WO-2017037479 A1 | | 3/2017 |
| WO | WO-2017041014 A1 | | 3/2017 |
| WO | WO-2017041385 A1 | | 3/2017 |
| WO | WO-2017041386 A1 | | 3/2017 |
| WO | WO-2017041387 A1 | | 3/2017 |
| WO | WO-2017119996 A1 | | 7/2017 |
| WO | WO-2017205728 A1 | | 11/2017 |
| WO | WO-2017214188 A1 | | 12/2017 |
| WO | WO-2018035612 A1 | | 3/2018 |
| WO | WO-2018060417 A1 | | 4/2018 |
| WO | WO-2018064569 A1 | | 4/2018 |
| WO | WO-2018115461 A1 | | 6/2018 |
| WO | WO-2018144938 A1 | | 8/2018 |
| WO | WO-2018144941 A1 | | 8/2018 |
| WO | WO-2018144943 A1 | | 8/2018 |
| WO | WO-2018144946 A1 | | 8/2018 |
| WO | WO-2018162728 A2 | | 9/2018 |
| WO | WO-2018185138 A1 | | 10/2018 |
| WO | WO-2018189265 A1 | | 10/2018 |
| WO | WO-2018209090 A1 | | 11/2018 |
| WO | WO-2018210692 A1 | | 11/2018 |
| WO | WO-2018211458 A1 | | 11/2018 |
| WO | WO-2018234443 A1 | | 12/2018 |
| WO | WO-2019020550 A2 | | 1/2019 |
| WO | WO-2019020551 A1 | | 1/2019 |
| WO | WO-2019020666 A1 | | 1/2019 |
| WO | WO-2019030384 A2 | | 2/2019 |
| WO | WO-2019048624 A1 | | 3/2019 |
| WO | WO-2019048626 A1 | | 3/2019 |
| WO | WO-2019048638 A1 | | 3/2019 |
| WO | WO-2019063481 A1 | | 4/2019 |
| WO | WO-2019063488 A2 | | 4/2019 |
| WO | WO-2019067264 A1 | | 4/2019 |
| WO | WO-2019072531 A1 | | 4/2019 |
| WO | WO-2019076967 A2 | | 4/2019 |
| WO | WO-2019096828 A1 | | 5/2019 |
| WO | WO-2019140441 A2 | | 7/2019 |
| WO | WO-2019140444 A1 | | 7/2019 |
| WO | WO-2019140448 A1 | | 7/2019 |
| WO | WO-2019140449 A1 | | 7/2019 |
| WO | WO-2019193141 A1 | | 10/2019 |
| WO | WO-2019216883 A1 | | 11/2019 |
| WO | WO-2019230183 A1 | | 12/2019 |
| WO | WO-2019238180 A1 | | 12/2019 |
| WO | WO-2019238181 A1 | | 12/2019 |
| WO | WO-2019238182 A1 | | 12/2019 |
| WO | WO-2019238195 A1 | | 12/2019 |
| WO | WO-2019238196 A1 | | 12/2019 |

(56) References Cited

FOREIGN PATENT DOCUMENTS

| WO | WO-2019238197 A1 | 12/2019 |
|---|---|---|
| WO | WO-2019238198 A1 | 12/2019 |
| WO | WO-2020002416 A1 | 1/2020 |
| WO | WO-2020018735 A1 | 1/2020 |
| WO | WO-2020043806 A1 | 3/2020 |
| WO | WO-2020139541 A1 | 7/2020 |
| WO | WO-2020157103 A1 | 8/2020 |
| WO | WO-2020159677 A1 | 8/2020 |
| WO | WO-2020167547 A1 | 8/2020 |
| WO | WO-2020242876 A1 | 12/2020 |
| WO | WO-2021059209 A1 | 4/2021 |

OTHER PUBLICATIONS

Bandodkar A.J., et al., "Battery-Free, Skin-Interfaced Microfluidic/Electronic Systems for Simultaneous Electrochemical, Colorimetric and Volumetric Analysis of Sweat," Science Advances, vol. 5 (1), Jan. 18, 2019, retrieved from http://advances.sciencemag.org/content/5/1/eaav3294, 16 pages.

Cauwe M., et al., "Technology Development for a Low-Cost, Roll-to-Roll Chip Embedding Solution Based on PET Foils," 18th European Microelectronics and Packaging Conference (EMPC), IEEE, Sep. 12, 2011, 6 pages.

Farooqui M.F., et al., "Low Cost Inkjet Printed Smart Bandage for Wireless Monitoring of Chronic Wounds," Scientific Reports, vol. 6, Jun. 29, 2016, 14 pages.

Geng Y., et al., "A Hybrid Low Power Biopatch for Body Surface Potential Measurement," IEEE Journal of Biomedical and Health Informatics, vol. 17, No. 3, May 1, 2013, pp. 591-599.

Iannetta Jr. R.A., et al., "Successful Case Histories of Polymer Based Circuitry on Flexible Film Substrates," Electro/94 International Conference Proceedings Combined vols. IEEE, XP010149465, May 10-12, 1994, pp. 885-889.

International Search Report and Written Opinion for Application No. PCT/EP2019/076049, mailed on Dec. 10, 2019, 12 pages.

Jinto G., et al., "Reliability of Plastic-Encapsulated Electronic Components in Supersaturated Steam Environments," IEEE Transactions on Components, Packaging and Manufacturing Technology, vol. 5 (10), Oct. 2015, pp. 1423-1431.

Little Miss Plasters, kidstravelclub.co.uk., retrieved from http://www.kidstravelclub.co.uk/little-miss-girls-childrens-plasters on Aug. 26, 2016, 2 pages.

Lu B., et al., "A Study of the Autofluorescence of Parylene Materials for μTAS Applications," Lab on Chip, vol. 10 (14), Jul. 2010, pp. 1826-1834.

McLeod A.J., et al., "Motion Magnification for Endoscopic Surgery," Progress in Biomedical Optics and Imaging, SPIE—International Society for Optical Engineering, Mar. 12, 2014, vol. 9036, 8 pages.

Mostafalu P., et al., "Wireless Flexible Smart Bandage for Continuous Monitoring Of Wound Oxygenation," IEEE Transactions on Biomedical Circuits and Systems, vol. 9 (5), Oct. 2015, pp. 670-677 (8 pages).

Narusawa H., "The Corona Discharge Causes Short Destruction that had Bad Influence on a Power Switching Circuit," Adphox Corporation, Jan. 1, 2009, retrieved from http://www.adphox.co.jp/keisokuki/ke-english-corona/CORONA_DISCHARGE_EN.pdf, 12 pages.

Raviglione A., et al., "Real-Time Smart Textile-Based System to Monitor Pressure Offloading of Diabetic Foot Ulcers," Journal of Diabetes Science and Technology, vol. 11 (5), Sep. 2017, pp. 894-898.

Rose D.P., et al., "Adhesive RFID Sensor Patch for Monitoring of Sweat Electrolytes," IEEE Transactions on Biomedical Engineering, vol. 62 (6), Jun. 2015, first published on Nov. 11, 2015, pp. 1457-1465.

Wakita J., et al., "Variations in Optical Absorption and Fluorescence Spectra for Polyimide Thin Films Caused by Structural Isomerism," Journal of Photopolymer Science and Technology, Jan. 1, 2003, 1 page.

Willis B., "Conformal Coating Inspection & Coating Faults," Vision Engineering, Jul. 21, 2016, retrieved from http://www.visioneng.com/wp-content/uploads/2017/11/Conformal-Coating-Inspection-and-Defects.21JUL16.pdf, 35 pages.

Willis B., "Guide to Conformal Coating & Cleaning Defects Contents," Mar. 1, 2014, retrieved from http://coatingguide.smartgroup.org/Files%20pdf/Coating%20Defects%20V2%20March2014.pdf, vol. 1, 31 pages.

International Preliminary Report on Patentability for Application No. PCT/EP2019/076049, mailed on Apr. 8, 2021, 9 pages.

Mehmood N., et al., "Applications Of Modern Sensors And Wireless Technology In Effective Wound Management: Modern Sensors And Wireless Technology," Journal of Biomedical Materials Research Part B, vol. 102, May 1, 2014, XP055739544, pp. 885-895.

\* cited by examiner

OPTICAL FIBERS FOR OPTICALLY SENSING THROUGH WOUND DRESSINGS

CROSS-REFERENCE TO RELATED APPLICATIONS

This application is a U.S. national stage application of International Patent Application No. PCT/EP2019/076049, filed Sep. 26, 2019, which claims priority to U.K. Provisional Application No. 1815854.3, filed on Sep. 28, 2018; the disclosures of which are hereby incorporated by reference in their entirety.

BACKGROUND

Field

The present disclosure relates at least to apparatuses, systems, and methods for the treatment of wounds, for example, using dressings in combination with negative pressure or non-negative pressure wound therapy.

Description of the Related Art

Many different types of wound dressings are known for aiding in the healing process of a human or animal. These different types of wound dressings include many different types of materials and layers, for example, gauze, pads, foam pads or multi-layer wound dressings. Topical negative pressure therapy, sometimes referred to as vacuum assisted closure, negative pressure wound therapy, or reduced pressure wound therapy, is widely recognized as a beneficial mechanism for improving the healing rate of a wound. Such therapy is applicable to a broad range of wounds such as incisional wounds, open wounds and abdominal wounds or the like.

Dressings for use in wound therapy, however, may provide little visualization or other information about the condition of a wound site beneath the dressings. As a result, in order to allow a clinician to inspect the healing or status of a wound, a dressing may be changed prematurely, such as before a desired level of wound healing has occurred or a full absorbent capacity of the dressings has been reached.

BRIEF DESCRIPTION OF THE DRAWINGS

Embodiments of the present disclosure will now be described hereinafter, by way of example only, with reference to the accompanying drawings in which.

SUMMARY

Figure 1:
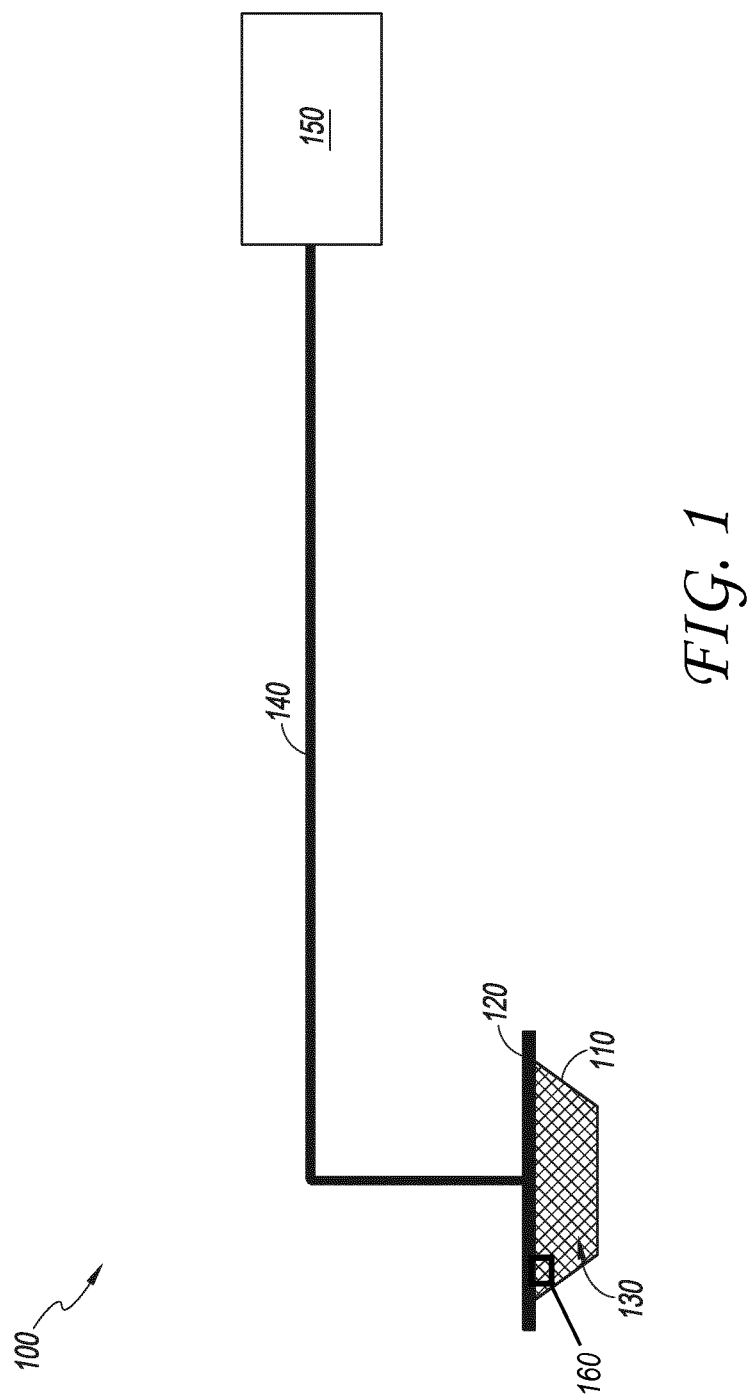
FIG. 1 illustrates an example negative pressure wound treatment system.

A wound treatment apparatus is disclosed herein that can include a wound dressing, a plurality of optical fibers, an emitter, a detector, and a processor. The wound dressing can be positioned proximate to a wound. The plurality of optical fibers can be positioned at least partly in the wound dressing and include a first optical fiber and a second optical fiber. The emitter can emit first electromagnetic radiation into the first optical fiber, and the first optical fiber can pass the first electromagnetic radiation. The detector can generate a signal responsive to second electromagnetic radiation exiting the second optical fiber and contacting the detector. The processor can determine a measurement value from the signal, and the measurement value can be indicative of a temperature of the wound or a pressure at the wound.

The wound treatment apparatus of the preceding paragraph can include one or more of the following features: The measurement value can be indicative of the pressure. The wound treatment apparatus can include a mechanochromic material configured to indicate the pressure. The measurement value can be indicative of the temperature, and the wound dressing can include a thermochromic material configured to change color responsive to the temperature. The wound treatment apparatus can include an optical thermometer configured to indicate the temperature, and the measurement value can be indicative of the temperature. The processor can control a pressure source responsive to the measurement value, and the pressure source can provide positive pressure or negative pressure to the wound. The processor can activate an indicator responsive to the measurement value. The emitter can be positioned proximate to an end of the first optical fiber. The first optical fiber can include a notch or a slit from which the first electromagnetic radiation exits the first optical fiber. The first electromagnetic radiation or the second electromagnetic radiation can have a wavelength between 300 nm and 2400 nm. An end of the first optical fiber can be truncated at an angle so that the first electromagnetic radiation exiting the end of the first optical fiber scatters. The wound dressing can include a wound filler and a wound cover, and the first optical fiber and the second optical fiber can extend through the wound filler and the wound cover. The emitter and the detector can be positioned within a non-sterile portion of the wound dressing. The wound treatment apparatus can include: a polarizer configured to polarize the first electromagnetic radiation passing through the first optical fiber; or a filter configured to filter the first electromagnetic radiation passing through the first optical fiber. The plurality of optical fibers can include a third optical fiber that can pass a different wavelength of electromagnetic radiation than the first optical fiber. The first optical fiber and the second optical fiber can extend parallel to a direction in which the wound dressing extends. The first optical fiber and the second optical fiber can extend perpendicular to a direction in which the wound dressing extends. The wound treatment apparatus can include a plurality of detectors including the detector, and the plurality of detectors can be positioned around the emitter. The second electromagnetic radiation can include a portion of the first electromagnetic radiation that reflected off of the wound.

A method is disclosed herein that can include: collecting exudate with a wound dressing positioned over a wound; emitting first electromagnetic radiation into a first optical fiber of a plurality of optical fibers, the plurality of optical fibers being positioned at least partly in the wound dressing; passing the first electromagnetic radiation with the first optical fiber; passing second electromagnetic radiation with a second optical fiber of the plurality of optical fibers; generating a signal responsive to the second electromagnetic radiation exiting the second optical fiber; and determining from the signal a measurement value indicative of a temperature of the wound or a pressure at the wound.

The method of the preceding paragraph can include one or more of the following features: The method can include indicating the pressure using a mechanochromic material, the measurement value being indicative of the pressure. The method can include changing a color of a thermochromic material responsive to the temperature, the measurement value being indicative of the temperature. The method can include indicating the temperature using an optical thermometer, the measurement value being indicative of the temperature. The method can include providing positive pressure or negative pressure to the wound responsive to the measurement value. The method can include activating an indicator responsive to the measurement value. The second electromagnetic radiation can include a portion of the first electromagnetic radiation that reflected off of the wound.

DETAILED DESCRIPTION

Overview

A wound dressing can include optical fibers (sometimes referred to as light pipes) that are integrated in the wound dressing and may, for example, be positioned in-plane or through-plane relative to the wound dressing. One or more of the optical fibers can transmit electromagnetic radiation (for instance, having a wavelength between about 300 nm and about 2400 nm, such as at 300 nm, 350 nm, 380 nm, 400 nm, 450 nm, 485 nm, 500 nm, 550 nm, 565 nm, 600 nm, 625 nm, 650 nm, 700 nm, 740 nm, 750 nm, 800 nm, 850 nm, 900 nm, 950 nm, 1000 nm, 1050 nm, 1100 nm, 1150 nm, 1200 nm, 1250 nm, 1300 nm, 1350 nm, 1400 nm, 1450 nm, 1500 nm, 1550 nm, 1600 nm, 1650 nm, 1700 nm, 1750 nm, 1800 nm, 1850 nm, 1900 nm, 1950 nm, 2000 nm, 2050 nm, 2100 nm, 2150 nm, 2200 nm, 2250 nm, 2300 nm, 2350 nm, or 2400 nm or in a range between two of the aforementioned wavelengths like between 300 nm to 600 nm, 380 nm to 500 nm, 400 nm to 700 nm, 450 nm to 485 nm, 500 nm to 565 nm, 600 nm to 900 nm, 625 nm to 740 nm, 800 nm to 1100 nm, 900 nm to 1200 nm, 1200 nm to 1500 nm, 1500 nm to 1800 nm, 1800 nm to 2100 nm, or 2100 nm to 2400 nm or in a range of visible light [such as blue light, green light, or red light] or infrared light) from one or more emitters (for example, light sources like light emitting diodes (LEDs)) to a wound underneath the wound dressing. The electromagnetic radiation passed by the optical fibers from the one or more emitters can scatter off of the wound, and the scattered electromagnetic radiation may be captured by one or more of the optical fibers and transmitted to one or more detectors. The output from the one or more detectors can desirably, in certain implementations, be used to investigate a condition of the wound without removing the wound dressing once placed over the wound.

The use of the optical fibers as disclosed herein can, in certain implementations, advantageously permit the delivery or detection of electromagnetic radiation from emitters or detectors that may be located away from the wound or safely isolated within the wound dressing. As a result, the emitters or detectors or other associated electronics can be located in a manner that reduces or limits an electrical safety risk from use of the emitters or detectors or other associated electronics.

The integration of optical fibers into or around a wound dressing can permit investigation of a wound by analyzing electromagnetic radiation returning from or around a wound. Such electromagnetic radiation can include information on a wound condition, color, temperature, pH, pressure, infection, among other possibilities. The investigation can be facilitated through use of one or more of (i) direct optical measurement or observation of a wound or local tissue, (ii) temperature identification by a color changing thermochromic material (where a change in color is associated with a change in temperature), (iii) optical identification of an absence of negative pressure generated by presence or absence of total internal reflection within an optical fiber, (iv) presence or absence of positive pressure (load) generated by mechanochromic (pressure-sensitive) material, (v) presence or absence of negative pressure generated by mechanochromic (pressure-sensitive) material, (vi) presence of positive pressure (load) generated by failure of the optical fiber material or loss of optical signal, (vii) multiplexing techniques whereby electromagnetic radiation is polarized for sectionable area interrogation, or (viii) optical measurement of pH by color changing pH sensitive materials, such as dyes or gels, and which may be encapsulated within a wound dressing.

Fiber optic tubes can run from emitters or detectors and allow electronics to be placed away from the wound and load bearing parts. The emitters and detectors can then have an optical path running out to the light pipes or all the way to a wound. The fiber optic tubes can include a polymer for encapsulation, silicone gel, or tubing.

The features described herein can provide one or more of the following advantages: the optical fibers can allow tighter light cones into a wound, electronics may not be positioned within a sterile portion of a wound dressing, electronics may not be positioned proximal to a wound that may also be exuding or challenged by liquid, electronics may not be positioned proximal to a wound and thus may not cause pressure points or introduce uneven topography near the wound, and electronics can be positioned proximal to a wound but pressure points or uneven topography may be shielded by an intermediary material.

The electromagnetic radiation emitted by an emitter can, for example, have one or more wavelengths between 300 nm and 2400 nm, such as at 300 nm, 350 nm, 380 nm, 400 nm, 450 nm, 485 nm, 500 nm, 550 nm, 565 nm, 600 nm, 625 nm, 650 nm, 700 nm, 740 nm, 750 nm, 800 nm, 850 nm, 900 nm, 950 nm, 1000 nm, 1050 nm, 1100 nm, 1150 nm, 1200 nm, 1250 nm, 1300 nm, 1350 nm, 1400 nm, 1450 nm, 1500 nm, 1550 nm, 1600 nm, 1650 nm, 1700 nm, 1750 nm, 1800 nm, 1850 nm, 1900 nm, 1950 nm, 2000 nm, 2050 nm, 2100 nm, 2150 nm, 2200 nm, 2250 nm, 2300 nm, 2350 nm, or 2400 nm or in a range between two of the aforementioned wavelengths (such as between 300 nm to 600 nm, 380 nm to 500 nm, 400 nm to 700 nm, 450 nm to 485 nm, 500 nm to 565 nm, 600 nm to 900 nm, 625 nm to 740 nm, 800 nm to 1100 nm, 900 nm to 1200 nm, 1200 nm to 1500 nm, 1500 nm to 1800 nm, 1800 nm to 2100 nm, or 2100 nm to 2400 nm) or in a range of visible light (such as blue light, green light, or red light) or infrared light, in some implementations. In other implementations, another one or more wavelengths of electromagnetic radiation may be emitted that is less than 300 nm or greater than 2400 nm. The emitter can cycle or transition between different wavelengths of electromagnetic radiation in order to obtain different measurements from or near a wound. There can be different optical fibers that may be constructed or assigned to emit electromagnetic radiation of different wavelengths. Further, one or more polarizers can polarize the electromagnetic radiation passing through the optical fibers or one or more filters can filter the electromagnetic radiation passing through the optical fibers.

Introduction

Aspects disclosed herein at least partly relate to apparatuses and methods of monitoring and treating biological tissue with sensor-enabled substrates. The aspects disclosed herein are not limited to treatment or monitoring of a particular type of tissue or injury, instead the sensor-enabled technologies disclosed herein are broadly applicable to any type of therapy that may benefit from sensor-enabled substrates. Some implementations utilize sensors and data collection relied upon by health care providers to make both diagnostic and patient management decisions.

Some aspects disclosed herein relate to the use of sensors mounted on or embedded within substrates configured to be used in the treatment of both intact and damaged human or animal tissue. Such sensors may collect information about the surrounding tissue and transmit such information to a computing device or a caregiver to be utilized in further treatment.

The sensor embodiments disclosed herein may be used in combination with clothing. Non-limiting examples of clothing for use with embodiments of the sensors disclosed herein include shirts, pants, trousers, dresses, undergarments, outer-garments, gloves, shoes, hats, and other suitable garments. In certain embodiments, the sensor embodiments disclosed herein may be welded into or laminated into/onto the particular garments. The sensor embodiments may be printed directly onto the garment and/or embedded into the fabric.

Sensor embodiments disclosed herein may be incorporated into cushioning or bed padding, such as within a hospital bed, to monitor patient characteristics, such as any characteristic disclosed herein.

The sensor embodiments disclosed herein may be utilized in rehabilitation devices and treatments, including sports medicine. For example, the sensor embodiments disclosed herein may be used in braces, sleeves, wraps, supports, and other suitable items. Similarly, the sensor embodiments disclosed herein may be incorporated into sporting equipment, such as helmets, sleeves, and/or pads.

The sensor embodiments disclosed herein may be used in coordination with surgical devices, for example, the NAVIO surgical system by Smith & Nephew Inc. In implementations, the sensor embodiments disclosed herein may be in communication with such surgical devices to guide placement of the surgical devices. To further aid in surgical techniques, the sensors disclosed herein may be incorporated into a surgical drape to provide information regarding tissue under the drape that may not be immediately visible to the naked eye.

Sensor embodiments as disclosed herein may also be utilized for pre-surgical assessment. For example, such sensor embodiments may be used to collect information about a potential surgical site, such as by monitoring skin and the underlying tissues for a possible incision site. For example, perfusion levels or other suitable characteristics may be monitored at the surface of the skin and deeper in the tissue to assess whether an individual patient may be at risk for surgical complications. Sensor embodiments such as those disclosed herein may be used to evaluate the presence of microbial infection and provide an indication for the use of antimicrobials. Further, sensor embodiments disclosed herein may collect further information in deeper tissue, such as identifying pressure ulcer damage or the fatty tissue levels.

The sensor embodiments disclosed herein may be utilized in cardiovascular monitoring. For example, such sensor embodiments may be incorporated into a flexible cardiovascular monitor that may be placed against the skin to monitor characteristics of the cardiovascular system and communicate such information to another device or a caregiver.

The sensor embodiments disclosed herein may be incorporated into implantable devices, such as implantable orthopedic implants, including flexible implants. Such sensor embodiments may be configured to collect information regarding the implant site and transmit this information to an external source.

Sensor embodiments as disclosed herein may be incorporated into Ear, Nose, and Throat (ENT) applications. For example, such sensor embodiments may be utilized to monitor recovery from ENT-related surgery, such as wound monitoring within the sinus passage.

As described in greater detail below, the sensor embodiments disclosed herein may encompass sensor printing technology with encapsulation, such as encapsulation with a polymer film Such a film may be constructed using any polymer described herein, such as polyurethane. Encapsulation of the sensor embodiments may provide waterproofing of the electronics and protection from local tissue, local fluids, and other sources of potential damage.

Embodiments disclosed herein at least partly relate to apparatuses and methods of treating a wound with or without reduced pressure, including for example a source of negative pressure and wound dressing components and apparatuses. The apparatuses and components comprising the wound overlay and packing materials or internal layers, if any, are sometimes collectively referred to herein as dressings. In some embodiments, the wound dressing can be provided to be utilized without reduced pressure.

Some embodiments disclosed herein relate to wound therapy for a human or animal body. Therefore, any reference to a wound herein can refer to a wound on a human or animal body, and any reference to a body herein can refer to a human or animal body. The disclosed technology embodiments may relate to preventing or minimizing damage to physiological tissue or living tissue, or to the treatment of damaged tissue (for example, a wound as described herein).

As used herein the expression "wound" may include an injury to living tissue may be caused by a cut, blow, or other impact, typically one in which the skin is cut or broken. A wound may be a chronic or acute injury. Acute wounds occur as a result of surgery or trauma. They move through the stages of healing within a predicted timeframe. Chronic wounds typically begin as acute wounds. The acute wound can become a chronic wound when it does not follow the healing stages resulting in a lengthened recovery. It is believed that the transition from acute to chronic wound can be due to a patient being immuno-compromised.

Chronic wounds may include for example: venous ulcers (such as those that occur in the legs), which account for the majority of chronic wounds and mostly affect the elderly, diabetic ulcers (for example, foot or ankle ulcers), peripheral arterial disease, pressure ulcers, or epidermolysis bullosa (EB).

Examples of other wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

Wounds may also include a deep tissue injury. Deep tissue injury is a term proposed by the National Pressure Ulcer Advisory Panel (NPUAP) to describe a unique form of pressure ulcers. These ulcers have been described by clinicians for many years with terms such as purple pressure ulcers, ulcers that are likely to deteriorate and bruises on bony prominences.

Wound may also include tissue at risk of becoming a wound as discussed herein. For example, tissue at risk may include tissue over a bony protuberance (at risk of deep tissue injury/insult) or pre-surgical tissue (for example, knee tissue) that may has the potential to be cut (for example, for joint replacement/surgical alteration/reconstruction).

Some aspects relate to methods of treating a wound with the technology disclosed herein in conjunction with one or more of the following: advanced footwear, turning a patient, offloading (such as, offloading diabetic foot ulcers), treatment of infection, systemix, antimicrobial, antibiotics, surgery, removal of tissue, affecting blood flow, physiotherapy, exercise, bathing, nutrition, hydration, nerve stimulation, ultrasound, electrostimulation, oxygen therapy, microwave therapy, active agents ozone, antibiotics, antimicrobials, or the like.

Alternatively or additionally, a wound may be treated using topical negative pressure and/or traditional advanced wound care, which is not aided by the using of applied negative pressure (may also be referred to as non-negative pressure therapy).

Advanced wound care may include use of an absorbent dressing, an occlusive dressing, use of an antimicrobial and/or debriding agents in a wound dressing or adjunct, a pad (for example, a cushioning or compressive therapy, such as stockings or bandages), or the like.

Treatment of such wounds can be performed using traditional wound care, wherein a dressing can be applied to the wound to facilitate and promote healing of the wound.

Some aspects relate to methods of manufacturing a wound dressing comprising providing a wound dressing as disclosed herein.

The wound dressings that may be utilized in conjunction with the disclosed technology include any known dressing in the art. The technology is applicable to negative pressure therapy treatment as well as non-negative pressure therapy treatment.

A wound dressing can include one or more absorbent layer(s). The absorbent layer may be a foam or a superabsorbent.

Wound dressings may comprise a dressing layer including a polysaccharide or modified polysaccharide, a polyvinylpyrrolidone, a polyvinyl alcohol, a polyvinyl ether, a polyurethane, a polyacrylate, a polyacrylamide, collagen, or gelatin or mixtures thereof. Dressing layers comprising the polymers listed are known in the art as being useful for forming a wound dressing layer for either negative pressure therapy or non-negative pressure therapy.

The polymer matrix may be a polysaccharide or modified polysaccharide.

The polymer matrix may be a cellulose. Cellulose material may include hydrophilically modified cellulose such as methyl cellulose, carboxymethyl cellulose (CMC), carboxymethyl cellulose (CEC), ethyl cellulose, propyl cellulose, hydroxyethyl cellulose, hydroxypropyl cellulose, hydroxypropylmethyl cellulose, carboxyethyl sulphonate cellulose, cellulose alkyl sulphonate, or mixtures thereof.

Cellulose material may be cellulose alkyl sulphonate. The alkyl moiety of the alkyl sulphonate substituent group may have an alkyl group having 1 to 6 carbon atoms, such as methyl, ethyl, propyl, or butyl. The alkyl moiety may be branched or unbranched, and hence suitable propyl sulphonate substituents may be 1- or 2-methyl-ethylsulphonate. Butyl sulphonate substituents may be 2-ethyl-ethylsulphonate, 2,2-dimethyl-ethylsulphonate, or 1,2-dimethyl-ethylsulphonate. The alkyl sulphonate substituent group may be ethyl sulphonate. The cellulose alkyl sulphonate is described in WO10061225, US2016/114074, US2006/0142560, or U.S. Pat. No. 5,703,225, the disclosures of which are hereby incorporated by reference in their entirety.

Cellulose alkyl sulfonates may have varying degrees of substitution, the chain length of the cellulose backbone structure, and the structure of the alkyl sulfonate substituent. Solubility and absorbency are largely dependent on the degree of substitution: as the degree of substitution is increased, the cellulose alkyl sulfonate becomes increasingly soluble. It follows that, as solubility increases, absorbency increases.

A wound dressing can also comprise a top or cover layer.

The thickness of the wound dressing disclosed herein may be between 1 to 20, or 2 to 10, or 3 to 7 mm.

Non-Negative Pressure Wound Dressing

The disclosed technology may be used in conjunction with a non-negative pressure dressing. A non-negative pressure wound dressing suitable for providing protection at a wound site may comprise:
an absorbent layer for absorbing wound exudate and
an obscuring element for at least partially obscuring a view of wound exudate absorbed by the absorbent layer in use.

The obscuring element may be partially translucent.

The obscuring element may be a masking layer.

The non-negative pressure wound dressing may further comprise a region in or adjacent the obscuring element for allowing viewing of the absorbent layer. For example, the obscuring element layer may be provided over a central region of the absorbent layer and not over a border region of the absorbent layer. The obscuring element can be of hydrophilic material or coated with a hydrophilic material.

The obscuring element may comprise a three-dimensional knitted spacer fabric. The spacer fabric is known in the art and may include a knitted spacer fabric layer.

The obscuring element may further comprise an indicator for indicating the need to change the dressing.

The obscuring element can be provided as a layer at least partially over the absorbent layer, further from a wound site than the absorbent layer in use.

The non-negative pressure wound dressing may further comprise a plurality of openings in the obscuring element for allowing fluid to move therethrough. The obscuring element may comprise, or may be coated with, a material having size-exclusion properties for selectively permitting or preventing passage of molecules of a predetermined size or weight.

The obscuring element may be configured to at least partially mask light radiation having wavelength of 600 nm and less.

The obscuring element may be configured to reduce light absorption by 50% or more.

The obscuring element may be configured to yield a CIE L* value of 50 or more, and optionally 70 or more. The obscuring element may be configured to yield a CIE L* value of 70 or more.

The non-negative pressure wound dressing may further comprise at least one of a wound contact layer, a foam layer, an odor control element, a pressure-resistant layer and a cover layer.

The cover layer is present, and the cover layer is a translucent film Typically, the translucent film has a moisture vapour permeability of 500 g/m$^2$/24 hours or more.

The translucent film may be a bacterial bather.

The non-negative pressure wound dressing as disclosed herein comprises the wound contact layer and the absorbent layer overlies the wound contact layer. The wound contact layer carries an adhesive portion for forming a substantially fluid tight seal over the wound site.

The non-negative pressure wound dressing as disclosed herein may comprise the obscuring element and the absorbent layer being provided as a single layer.

The non-negative pressure wound dressing disclosed herein can comprise the foam layer, and the obscuring element is of a material comprising components that may be displaced or broken by movement of the obscuring element.

The non-negative pressure wound dressing can comprise an odor control element or may not include an odor control element. When present, the odor control element may be dispersed within or adjacent the absorbent layer or the obscuring element. Alternatively, when present the odor control element may be provided as a layer sandwiched between the foam layer and the absorbent layer.

The disclosed technology for a non-negative pressure wound dressing can comprise a method of manufacturing a wound dressing, comprising: providing an absorbent layer for absorbing wound exudate; and providing an obscuring element for at least partially obscuring a view of wound exudate absorbed by the absorbent layer in use.

The non-negative pressure wound dressing may be suitable for providing protection at a wound site, comprising: an absorbent layer for absorbing wound exudate; and a shielding layer provided over the absorbent layer, and further from a wound-facing side of the wound dressing than the absorbent layer. The shielding layer may be provided directly over the absorbent layer. The shielding layer can comprise a three-dimensional spacer fabric layer.

The shielding layer increases the area over which a pressure applied to the dressing is transferred by 25% or more or the initial area of application. For example the shielding layer increases the area over which a pressure applied to the dressing is transferred by 50% or more, and optionally by 100% or more, and optionally by 200% or more.

The shielding layer may comprise 2 or more sub-layers, wherein a first sub-layer comprises through holes and a further sub-layer comprises through holes and the through holes of the first sub-layer are offset from the through holes of the further sub-layer.

The non-negative pressure wound dressing as disclosed herein may further comprise a permeable cover layer for allowing the transmission of gas and vapour therethrough, the cover layer provided over the shielding layer, wherein through holes of the cover layer are offset from through holes of the shielding layer.

The non-negative pressure wound dressing may be suitable for treatment of pressure ulcers.

A more detailed description of the non-negative pressure dressing disclosed hereinabove is provided in WO2013007973, the entirety of which is hereby incorporated by reference.

The non-negative pressure wound dressing may be a multi-layered wound dressing comprising: a fibrous absorbent layer for absorbing exudate from a wound site; and a support layer configured to reduce shrinkage of at least a portion of the wound dressing.

The multi-layered wound dressing disclosed herein, further can comprise a liquid impermeable film layer, wherein the support layer is located between the absorbent layer and the film layer.

The support layer disclosed herein may comprise a net. The net may comprise a geometric structure having a plurality of substantially geometric apertures extending therethrough. The geometric structure may for example comprise a plurality of bosses substantially evenly spaced and joined by polymer strands to form the substantially geometric apertures between the polymer strands.

The net may be formed from high density polyethylene.

The apertures may have an area from 0.005 to 0.32 mm$^2$.

The support layer may have a tensile strength from 0.05 to 0.06 Nm.

The support layer may have a thickness of from 50 to 150 μm.

The support layer may be located directly adjacent the absorbent layer. Typically, the support layer is bonded to fibers in a top surface of the absorbent layer. The support layer may further comprise a bonding layer, wherein the support layer is heat laminated to the fibers in the absorbent layer via the bonding layer. The bonding layer may comprise a low melting point adhesive such as ethylene-vinyl acetate adhesive.

The multi-layered wound dressing disclosed herein further can comprise an adhesive layer attaching the film layer to the support layer.

The multi-layered wound dressing disclosed herein further can comprise a wound contact layer located adjacent the absorbent layer for positioning adjacent a wound. The multi-layered wound dressing may further comprise a fluid transport layer between the wound contact layer and the absorbent layer for transporting exudate away from a wound into the absorbent layer.

A more detailed description of the multi-layered wound dressing disclosed hereinabove is provided in International Patent Application Publication No. WO2018077872 published on 3 May 2018, the entirety of which is hereby incorporated by reference.

The disclosed technology may be incorporated in a wound dressing comprising a vertically lapped material comprising: a first layer of an absorbing layer of material, and a second layer of material, wherein the first layer being constructed from at least one layer of non-woven textile fibers, the non-woven textile fibers being folded into a plurality of folds to form a pleated structure. The wound dressing further can comprise a second layer of material that is temporarily or permanently connected to the first layer of material.

Typically the vertically lapped material has been slitted.

The first layer can have a pleated structure having a depth determined by the depth of pleats or by the slitting width. The first layer of material may be a moldable, lightweight, fiber-based material, blend of material or composition layer.

The first layer of material may comprise one or more of manufactured fibers from synthetic, natural or inorganic polymers, natural fibers of a cellulosic, proteinaceous or mineral source.

The wound dressing may comprise two or more layers of the absorbing layer of material vertically lapped material stacked one on top of the other, wherein the two or more layers have the same or different densities or composition.

The wound dressing may comprise only one layer of the absorbing layer of material vertically lapped material.

The absorbing layer of material is a blend of natural or synthetic, organic or inorganic fibers, and binder fibers, or bicomponent fibers typically PET with a low melt temperature PET coating to soften at specified temperatures and to act as a bonding agent in the overall blend.

The absorbing layer of material may be a blend of 5 to 95% thermoplastic polymer, and 5 to 95 wt % of a cellulose or derivative thereof.

The wound dressing disclosed herein can have a second layer comprises a foam or a dressing fixative.

The foam may be a polyurethane foam. The polyurethane foam may have an open or closed pore structure.

The dressing fixative may include bandages, tape, gauze, or backing layer.

The wound dressing as disclosed herein can comprise the absorbing layer of material connected directly to a second layer by lamination or by an adhesive, and the second layer is connected to a dressing fixative layer. The adhesive may be an acrylic adhesive, or a silicone adhesive.

The wound dressing as disclosed herein further can comprise layer of a superabsorbent fiber, or a viscose fiber or a polyester fiber.

The wound dressing as disclosed herein further can comprise a backing layer. The backing layer may be a transparent or opaque film Typically the backing layer comprises a polyurethane film (typically a transparent polyurethane film).

A more detailed description of the multi-layered wound dressing disclosed herein is provided in International Patent Application Publication No. WO2018108784, the entirety of which is hereby incorporated by reference.

The non-negative pressure wound dressing may comprise an absorbent component for a wound dressing, the component comprising a wound contacting layer comprising gel forming fibers bound to a foam layer, wherein the foam layer is bound directly to the wound contact layer by an adhesive, polymer based melt layer, by flame lamination or by ultrasound.

The absorbent component may be in a sheet form.

The wound contacting layer may comprise a layer of woven or non-woven or knitted gel forming fibers.

The foam layer may be an open cell foam, or closed cell foam, typically an open cell foam. The foam layer is a hydrophilic foam.

The wound dressing may comprise the component that forms an island in direct contact with the wound surrounded by periphery of adhesive that adheres the dressing to the wound. The adhesive may be a silicone or acrylic adhesive, typically a silicone adhesive.

The wound dressing may be covered by a film layer on the surface of the dressing furthest from the wound.

A more detailed description of the wound dressing of this type hereinabove is provided in EP2498829, the entirety of which is hereby incorporated by reference.

The non-negative pressure wound dressing may comprise a multi layered wound dressing for use on wounds producing high levels of exudate, characterized in that the dressing comprising: a transmission layer having an MVTR of at least 300 gm$^2$/24 hours, an absorbent core comprising gel forming fibers capable of absorbing and retaining exudate, a wound contacting layer comprising gel forming fibers which transmits exudate to the absorbent core and a keying layer positioned on the absorbent core, the absorbent core and wound contacting layer limiting the lateral spread of exudate in the dressing to the region of the wound.

The wound dressing may be capable of handling at least 6 g (or 8 g and 15 g) of fluid per 10 cm$^2$ of dressing in 24 hours.

The wound dressing may comprise gel forming fibers that are chemically modified cellulosic fibers in the form of a fabric. The fibers may include carboxymethylated cellulose fibers, typically sodium carboxymethylcellulose fiber.

The wound dressing may comprise a wound contact layer with a lateral wicking rate from 5 mm per minute to 40 mm per minute. The wound contact layer may have a fiber density between 25 gm$^2$ and 55 gm$^2$, such as 35 gm$^2$.

The absorbent core may have an absorbency of exudate of at least 10 g/g, and typically a rate of lateral wicking of less the 20 mm per minute.

The absorbent core may have a blend in the range of up to 25% cellulosic fibers by weight and 75% to 100% gel forming fibers by weight.

Alternatively, the absorbent core may have a blend in the range of up to 50% cellulosic fibers by weight and 50% to 100% gel forming fibers by weight. For example the blend is in the range of 50% cellulosic fibers by weight and 50% gel forming fibers by weight.

The fiber density in the absorbent core may be between 150 gm$^2$ and 250 gm$^2$, or about 200 gm$^2$.

The wound dressing when wet may have shrinkage that is less than 25% or less than 15% of its original size/dimension.

The wound dressing may comprise a transmission layer and the layer is a foam. The transmission layer may be a polyurethane foam laminated to a polyurethane film.

The wound dressing may comprise one or more layers selected from the group comprising a soluble medicated film layer; an odor-absorbing layer; a spreading layer and an additional adhesive layer.

The wound dressing may be 2 mm and 4 mm thick.

The wound dressing may be characterized in that the keying layer bonds the absorbent core to a neighboring layer. The keying layer may be positioned on either the wound facing side of the absorbent core or the non-wound facing side of the absorbent core. The keying layer can be positioned between the absorbent core and the wound contact layer. The keying layer may be a polyamide web.

A more detailed description of the wound dressing of this type hereinabove is provided in EP1718257, the entirety of which is hereby incorporated by reference.

The non-negative pressure wound dressing may be a compression bandage. Compression bandages are known for use in the treatment of oedema and other venous and lymphatic disorders, e.g., of the lower limbs.

A compression bandage systems typically employ multiple layers including a padding layer between the skin and the compression layer or layers. The compression bandage may be useful for wounds such as handling venous leg ulcers.

The compression bandage may comprise a bandage system comprising an inner skin facing layer and an elastic outer layer, the inner layer comprising a first ply of foam and a second ply of an absorbent nonwoven web, the inner layer and outer layer being sufficiently elongated so as to be capable of being wound about a patient's limb. A compression bandage of this type is disclosed in WO99/58090, the entirety of which is hereby incorporated by reference.

The compression bandage system comprises: a) an inner skin facing, elongated, elastic bandage comprising: (i) an elongated, elastic substrate, and (ii) an elongated layer of foam, said foam layer being affixed to a face of said substrate and extending 33% or more across said face of substrate in transverse direction and 67% or more across said face of substrate in longitudinal direction; and b) an outer, elongated, self-adhering elastic bandage; said bandage having a compressive force when extended; wherein, in use, said foam layer of the inner bandage faces the skin and the outer bandage overlies the inner bandage. A compression bandage of this type is disclosed in WO2006/110527, the entirety of which is hereby incorporated by reference.

Other compression bandage systems, such as those disclosed in U.S. Pat. No. 6,759,566 and US 2002/0099318, the entirety of each of which is hereby incorporated by reference, may be used with features disclosed herein.

Negative Pressure Wound Dressing

Treatment of such wounds can be performed using negative pressure wound therapy, wherein a reduced or negative pressure can be applied to the wound to facilitate and promote healing of the wound. It will also be appreciated that the wound dressing and methods as disclosed herein may be applied to other parts of the body, and are not necessarily limited to treatment of wounds.

It will be understood that aspects of the present disclosure are generally applicable to use in topical negative pressure ("TNP") therapy systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

Negative pressure therapy can be used for the treatment of open or chronic wounds that are too large to spontaneously close or otherwise fail to heal by means of applying negative pressure to the site of the wound. Topical negative pressure (TNP) therapy or negative pressure wound therapy (NPWT) involves placing a cover that is impermeable or semipermeable to fluids over the wound, using various means to seal the cover to the tissue of the patient surrounding the wound, and connecting a source of negative pressure (such as a vacuum pump) to the cover in a manner so that negative pressure is created and maintained under the cover. It is believed that such negative pressures promote wound healing by facilitating the formation of granulation tissue at the wound site and assisting the body's normal inflammatory process while simultaneously removing excess fluid, which may contain adverse cytokines or bacteria.

Some of the dressings used in NPWT can include many different types of materials and layers, for example, gauze, pads, foam pads or multi-layer wound dressings. One example of a multi-layer wound dressing is the PICO dressing, available from Smith & Nephew, includes a wound contact layer and a superabsorbent layer beneath a backing layer to provide a canister-less system for treating a wound with NPWT. The wound dressing may be sealed to a suction port providing connection to a length of tubing, which may be used to pump fluid out of the dressing or to transmit negative pressure from a pump to the wound dressing. Additionally, RENASYS-F, RENASYS-G, RENASYS-AB, and RENASYS-F/AB, available from Smith & Nephew, are additional examples of NPWT wound dressings and systems. Another example of a multi-layer wound dressing is the ALLEVYN Life dressing, available from Smith & Nephew, which includes a moist wound environment dressing that is used to treat the wound without the use of negative pressure.

As is used herein, reduced or negative pressure levels, such as $-X$ mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of $-X$ mmHg reflects absolute pressure that is X mmHg below 760 mmHg or, in other words, an absolute pressure of (760−X) mmHg In addition, negative pressure that is "less" or "smaller" than X mmHg corresponds to pressure that is closer to atmospheric pressure (such as, $-40$ mmHg is less than $-60$ mmHg). Negative pressure that is "more" or "greater" than $-X$ mmHg corresponds to pressure that is further from atmospheric pressure (such as, $-80$ mmHg is more than $-60$ mmHg). Local ambient atmospheric pressure can be used as a reference point, and such local atmospheric pressure may not necessarily be, for example, 760 mmHg.

The negative pressure range for some aspects of the present disclosure can be approximately $-80$ mmHg, or between about $-20$ mmHg and $-200$ mmHg Note that these pressures are relative to normal ambient atmospheric pressure, which can be 760 mmHg. Thus, $-200$ mmHg would be about 560 mmHg in practical terms. In some embodiments, the pressure range can be between about $-40$ mmHg and $-150$ mmHg. Alternatively a pressure range of up to $-75$ mmHg, up to $-80$ mmHg or over $-80$ mmHg can be used. Also in other embodiments a pressure range of below $-75$ mmHg can be used. Alternatively, a pressure range of over approximately $-100$ mmHg, or even $-150$ mmHg, can be supplied by the negative pressure apparatus.

In some aspects of wound closure devices described herein, increased wound contraction can lead to increased tissue expansion in the surrounding wound tissue. This effect may be increased by varying the force applied to the tissue, for example, by varying the negative pressure applied to the wound over time, possibly in conjunction with increased tensile forces applied to the wound. Negative pressure may be varied over time for example using a sinusoidal wave, square wave, or in synchronization with one or more patient physiological indices (such as, heartbeat). Examples of such applications where additional disclosure relating to the preceding may be found include U.S. Pat. No. 8,235,955, titled "Wound treatment apparatus and method," issued on Aug. 7, 2012; and U.S. Pat. No. 7,753,894, titled "Wound cleansing apparatus with stress," issued Jul. 13, 2010. The disclosures of both of these patents are hereby incorporated by reference in their entirety.

The wound dressings, wound dressing components, wound treatment apparatuses and methods described herein may also be used in combination or in addition to those described in International Application No. PCT/IB2013/001469, filed May 22, 2013, published as WO 2013/175306 A2 on Nov. 28, 2013, titled "APPARATUSES AND METHODS FOR NEGATIVE PRESSURE WOUND THERAPY," U.S. patent application Ser. No. 14/418,908, filed Jan. 30, 2015, published as US 2015/0190286 A1 on Jul. 9, 2015, titled "WOUND DRESSING AND METHOD OF TREATMENT," the disclosures of which are hereby incorporated by reference in their entireties. The wound dressings, wound dressing components, wound treatment apparatuses and methods described herein may also be used in combination or in addition to those described in U.S. patent application Ser. No. 13/092,042, filed Apr. 21, 2011, published as US2011/0282309, titled "WOUND DRESSING AND METHOD OF USE," and U.S. patent application Ser. No. 14/715,527, filed May 18, 2015, published as US2016/0339158 A1 on Nov. 24, 2016, titled "FLUIDIC CONNECTOR FOR NEGATIVE PRESSURE WOUND THERAPY," the disclosure of each of which is hereby incorporated by reference in its entirety, including further details relating to wound dressings, the wound dressing components and principles, and the materials used for the wound dressings.

Additionally, some aspects related to TNP wound treatment comprising a wound dressing in combination with a pump or associated electronics described herein may also be used in combination or in addition to those described in International Application PCT/EP2016/059329 filed Apr. 26, 2016, published as WO 2016/174048 on Nov. 3, 2016, entitled "REDUCED PRESSURE APPARATUS AND METHODS," the disclosure of which is hereby incorporated by reference in its entirety.

Wound Dressing with Sensors

A wound dressing that incorporates a number of sensors can be utilized in order to monitor characteristics of a wound as it heals. Collecting data from the wounds that heal well, and from those that do not, can provide useful insights towards identifying characteristics to indicate whether a wound may be on a healing trajectory.

In some implementations, a number of sensor technologies can be used in wound dressings or one or more components forming part of an overall wound dressing apparatus.

Optical sensors can be used to measure wound appearance using an RGB sensor with an illumination source. Both the RGB sensor and the illumination source would be pressed up against the skin, such that light would penetrate into the tissue and take on the spectral features of the tissue itself.

Light propagation in tissue can be dominated by two major phenomena, scattering and attenuation. For attenuation, as light passes through tissue, its intensity may be lost due to absorption by various components of the tissue. Blue light tends to be attenuated heavily, whilst light at the red end of the spectrum tends to be attenuated least.

Scattering processes can be more complex, and can have various "regimes" which must be considered. The first aspect of scattering is based on the size of the scattering center compared with the wavelength of incident light. If the scattering center is much smaller than the wavelength of light, then Rayleigh scattering can be assumed. If the scattering center is on the order of the wavelength of light, then a more detailed Mie scattering formulation may be considered. Another factor involved in scattering light is the distance between input and output of the scattering media. If a mean free path of the light (the distance between scattering events) is much larger than the distance travelled, then ballistic photon transport may be assumed. In the case of tissue, scatting events are approximately 100 microns apart—so a 1 mm path distance would effectively randomize the photon direction and the system would enter a diffusive regime.

Ultra bright LEDs, an RGB sensor, and polyester optical filters can be used as components of the optical sensors to measure through tissue color differentiation. For example, because surface color can be measured from reflected light, a color can be measured from light which has passed through the tissue first for a given geometry. This can include color sensing from diffuse scattered light, from a LED in contact with the skin. A LED can be used with an RGB sensor nearby to detect the light which has diffused through the tissue. The optical sensors can image with diffuse internal light or surface reflected light.

Additionally, the optical sensors can be used to measure autofluorescence. Autoflourescense is used because the tissue is absorbing light at one wavelength, and emitting at another. Additionally, dead tissue may not auto-fluoresce and so this could be a very strong indication as to if the tissue is healthy or not. Due to blue light (or even ultraviolet light) having such a short penetration depth, it may be very useful for example to have a ultraviolet light with a red sensitive photodiode nearby (or some other wavelength shifted band) to act as a binary test for healthy tissue, which would auto-fluoresce at a very particular wavelength.

Wound Therapy System

FIG. 1 illustrates a negative or reduced pressure wound treatment (or TNP) system 100 comprising a wound filler 130 placed inside a wound cavity 110, the wound cavity sealed by a wound cover 120. The wound filler 130 in combination with the wound cover 120 can be referred to as a wound dressing. A single or multi lumen tube or conduit 140 is connected the wound cover 120 with a pump assembly 150 configured to supply reduced pressure. The wound cover 120 can be in fluidic communication with the wound cavity 110. A sensing element 160 (for example, a sensor or a sensing material like a mechanochromic material, a thermochromic material, or a pH sensitive material) can be proximate to, attached to, or incorporated in the wound cavity 110, the wound cover 120, the wound filler 130, or the conduit 140 and be used, for instance, to monitor the wound cavity 110 as described herein.

As illustrated in FIG. 1, the pump assembly 150 can be a canisterless pump assembly (meaning that exudate is collected in the wound dressing or is transferred via conduit 140 for collection to another location). However, any of the pump assemblies disclosed herein can be configured to include or support a canister. Additionally, any of the pump assemblies can be mounted to or supported by the dressing, or adjacent to the dressing.

The wound filler 130 can be any suitable type, such as hydrophilic or hydrophobic foam, gauze, inflatable bag, and so on. The wound filler 130 can be conformable to the wound cavity 110 such that it substantially fills the cavity. The wound cover 120 can provide a substantially fluid impermeable seal over the wound cavity 110. The wound cover 120 can have a top side and a bottom side, and the bottom side adhesively (or in any other suitable manner) seals with wound cavity 110. The conduit 140 or lumen or any other conduit or lumen disclosed herein can be formed from polyurethane, PVC, nylon, polyethylene, silicone, or any other suitable material.

The wound cover 120 can have a port (not shown) configured to receive an end of the conduit 140. For example, the port can be Renays Soft Port available from Smith & Nephew. Additionally or alternatively, the conduit 140 can pass through or under the wound cover 120 to supply reduced pressure to the wound cavity 110 so as to maintain a desired level of reduced pressure in the wound cavity. The conduit 140 can be any suitable article configured to provide at least a substantially sealed fluid flow pathway between the pump assembly 150 and the wound cover 120, so as to supply the reduced pressure provided by the pump assembly 150 to wound cavity 110.

The wound cover 120 and the wound filler 130 can be provided as a single article or an integrated single unit. In some implementations, no wound filler is provided and the wound cover by itself may be considered the wound dressing. The wound dressing may then be connected, via the conduit 140, to a source of negative pressure, such as the pump assembly 150. The pump assembly 150 can be miniaturized and portable, although larger conventional pumps such can also be used.

The wound cover 120 can be located over a wound site to be treated. The wound cover 120 can form a substantially sealed cavity or enclosure over the wound site. The wound cover 120 can be configured to have a film having a high water vapour permeability to enable the evaporation of surplus fluid, and can have a superabsorbing material contained therein to safely absorb wound exudate. It will be appreciated that throughout this specification reference is made to a wound. In this sense it is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. The components of the TNP system described herein can be particularly suited for incisional wounds that exude a small amount of wound exudate.

Some implementations of the system are designed to operate without the use of an exudate canister. Some implementations can be configured to support an exudate canister. Configuring the pump assembly 150 and conduit 140 so that the conduit 140 can be quickly and easily removed from the pump assembly 150 can facilitate or improve the process of dressing or pump changes, if necessary. Any of the pumps disclosed herein can be configured to have any suitable connection between the tubing and the pump.

The pump assembly 150 can be configured to deliver negative pressure of approximately −80 mmHg, or between about −20 mmHg and 200 mmHg in some implementations. Note that these pressures are relative to normal ambient atmospheric pressure thus, −200 mmHg would be about 560 mmHg in practical terms. The pressure range can be between about −40 mmHg and −150 mmHg. Alternatively a pressure range of up to −75 mmHg, up to −80 mmHg or over −80 mmHg can be used. Also a pressure range of below −−75 mmHg can be used. Alternatively a pressure range of over approximately −100 mmHg, or even 150 mmHg, can be supplied by the pump assembly 150.

In operation, the wound filler 130 is inserted into the wound cavity 110 and wound cover 120 is placed so as to seal the wound cavity 110. The pump assembly 150 provides a source of a negative pressure to the wound cover 120, which is transmitted to the wound cavity 110 via the wound filler 130. Fluid (such as, wound exudate) is drawn through the conduit 140, and can be stored in a canister. Fluid can be absorbed by the wound filler 130 or one or more absorbent layers (not shown).

Wound dressings that may be utilized with the pump assembly and other aspects of the present application include Renasys-F, Renasys-G, Renasys AB, and Pico Dressings available from Smith & Nephew. Further description of such wound dressings and other components of a negative pressure wound therapy system that may be used with the pump assembly and other aspects of the present application are found in U.S. Patent Publication Nos. 2011/0213287, 2011/0282309, 2012/0116334, 2012/0136325, and 2013/0110058, which are incorporated by reference in their entirety. Other suitable wound dressings can be utilized.

Figure 2:
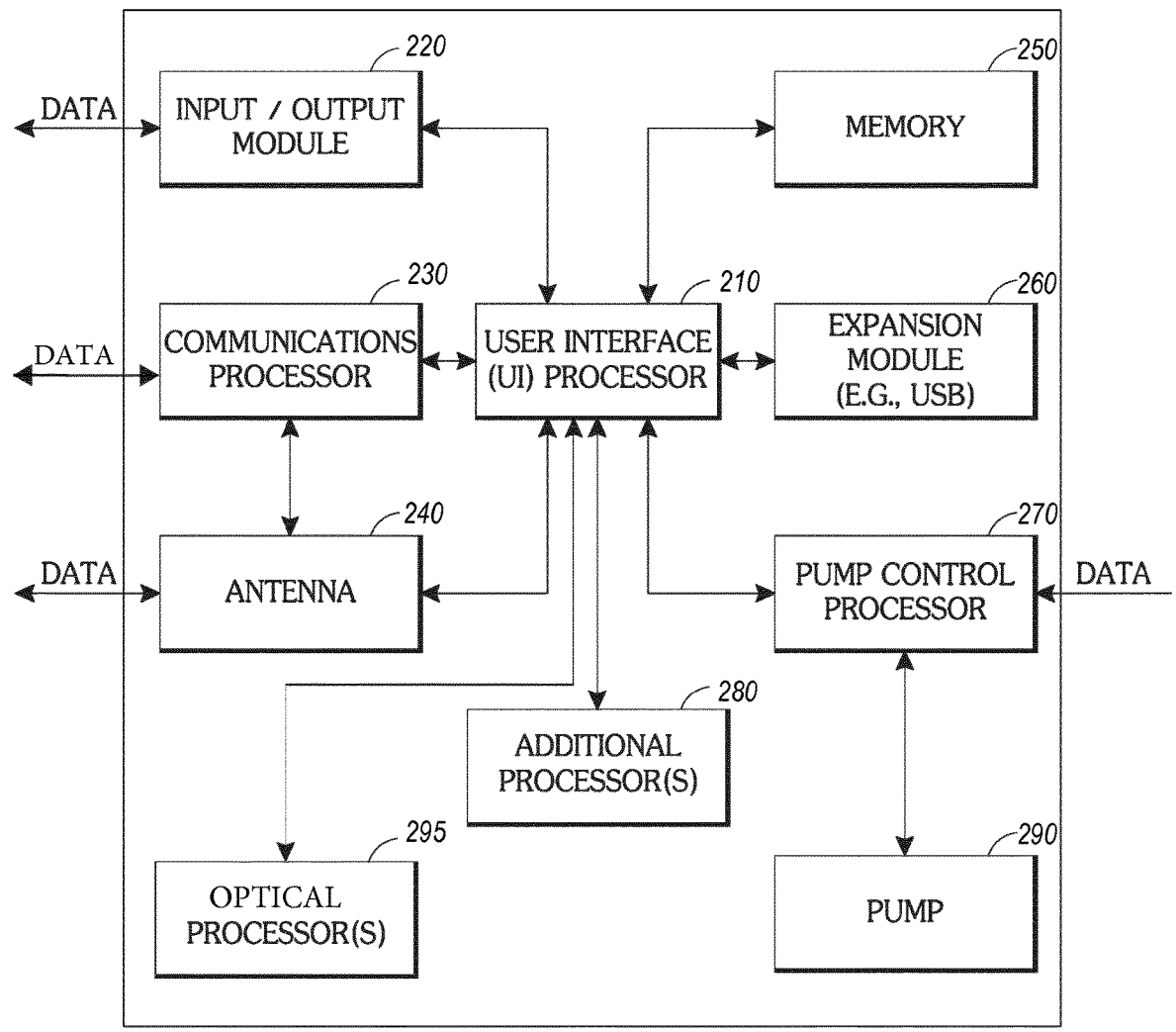
FIG. 2 illustrates an electrical component schematic of an example pump assembly.

FIG. 2 illustrates an electrical component schematic of a pump assembly 200. Electrical components can operate to accept user input, provide output to the user, operate the pump assembly and the TNP system, provide network connectivity, and so on. Electrical components can be mounted on one or more printed circuit boards (PCBs) that mechanically support and electrically connect electronic components using conductive tracks, pads and other features etched from copper sheets laminated onto a non-conductive substrate. Components, such as capacitors, resistors, or active devices, can be soldered on the PCBs or embedded in the substrate. As is illustrated, the pump assembly can include multiple processors.

The pump assembly can include a user interface controller or processor 10 that can function as a main processor and be configured to operate one or more components for accepting user input and providing output to the user, such as a display, buttons, etc. Input to the pump assembly and output from the pump assembly can controlled by an input/output (I/O) module 220. For example, the I/O module can receive data from one or more ports, such as serial, parallel, hybrid ports, and the like. The processor 210 also receives data from and provides data to one or more expansion modules 260, such as one or more USB ports, SD ports, CD drives, DVD drives, FireWire ports, Thunderbolt ports, PCI Express ports, and the like. The processor 210, along with other controllers or processors, stores data in memory 250, which can be one or more memory modules and be internal or external to the processor 210. Any suitable type of memory can be used, including volatile or non-volatile memory, such as RAM, ROM, magnetic memory, solid-state memory, magnetoresistive random-access memory (MRAM), and the like.

The processor 210 can be a general purpose controller, such as a low-power processor. The processor 210 can be an application specific processor. The processor 210 can be configured as a "central" processor in the electronic architecture of the pump assembly, and the processor 210 can coordinate the activity of other processors, such as a pump control processor 270, communications processor 230, and one or more additional processors 280 (e.g., processor for controlling the display 206, processor for controlling the buttons 212, etc.). The processor 210 can run a suitable operating system, such as a Linux, Windows CE, VxWorks, etc.

The pump control processor 270 can be configured to control the operation of a pump 290, such as a negative pressure pump. The pump 290 can be a suitable pump, such as a diaphragm pump, peristaltic pump, rotary pump, rotary vane pump, scroll pump, screw pump, liquid ring pump, diaphragm pump operated by a piezoelectric transducer, voice coil pump, and the like. The pump control processor 270 can measure pressure in a fluid flow path, using data received from one or more pressure sensors, calculate the rate of fluid flow, and control the pump. The pump control processor 270 can control a pump motor so that a desired level of negative pressure is achieved in the wound cavity 110. The desired level of negative pressure can be pressure set or selected by the user. The pump control processor 270 controls the pump (e.g., pump motor) using pulse-width modulation (PWM). A control signal for driving the pump can be a 0-100% duty cycle PWM signal. The pump control processor 270 can perform flow rate calculations and detect various conditions in a flow path. The pump control processor 270 can communicate information to the processor 210. The pump control processor 270 can include internal memory or can utilize memory 250. The pump control processor 270 can be a low-power processor.

A communications processor 230 can be configured to provide wired or wireless connectivity. The communications processor 230 can utilize one or more antennas 240 for sending and receiving data. The communications processor 230 can provide one or more of the following types of connections: Global Positioning System (GPS) technology, cellular connectivity (e.g., 2G, 3G, LTE, 4G), WiFi connectivity, Internet connectivity, and the like. Connectivity can be used for various activities, such as pump assembly location tracking, asset tracking, compliance monitoring, remote selection, uploading of logs, alarms, and other operational data, and adjustment of therapy settings, upgrading of software or firmware, and the like. The communications processor 230 can provide dual GPS/cellular functionality. Cellular functionality can, for example, be 3G functionality. The pump assembly can include a SIM card, and SIM-based positional information can be obtained.

The communications processor 230 can also be electrically coupled to one or more one or more serial, parallel, or hybrid data transfer connector interfaces through which the communications processor 230 can directly receive data or commands without receiving the data or commands through or from the processor 210. For instance, the data transfer connector interfaces can include one or more USB ports, SD ports, CD drives, DVD drives, FireWire ports, Thunderbolt ports, PCI Express ports, and the like.

The communications processor 230 can communicate information to the processor 210 and receive information from the processor 210. The communications processor 230 can include internal memory or can utilize memory 250. The communications processor 230 can be a low-power processor.

Using the connectivity provided by the communications processor 230, the device can upload any of the data stored, maintained, or tracked by the pump assembly. The device can also download various operational data, such as therapy selection and parameters, firmware and software patches and upgrades, and the like.

An optical processor 295 can process optical signals generated by a detector to determine a measurement value indicative of wound characteristics (e.g., temperature, pressure, or exudate features). The optical processor 295 can be communicatively coupled with an emitter for emitting electromagnetic radiation and the detector for sensing electromagnetic radiation. The optical processor 295 can control the emission of electromagnetic radiation with the emitter. Further, the optical processor 295 can process the optical signals generated by the detector and output characteristics of a wound based on the information determined from the optical signals. The optical processor 295 can include internal memory (not shown) or can utilize memory 250. The optical processor 295 can access the internal memory or the memory 250 in forming associations between data received from the detector and wound characteristics. The optical processor 295 can communicate information, such as measurement values or other determined information, to the processor 210.

Figure 3:
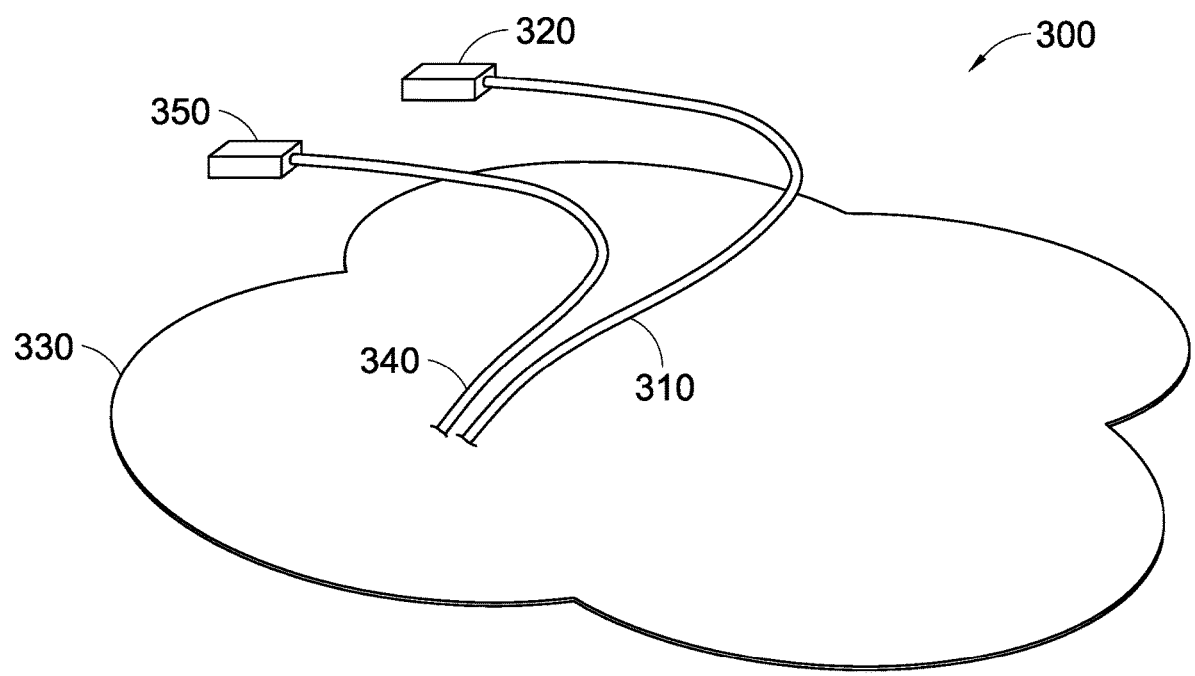
FIG. 3 illustrates an example wound treatment apparatus including an emitter, a detector, and multiple optical fibers.

FIG. 3 illustrates the wound treatment apparatus 300 including one or more optical fibers. The wound treatment apparatus 300 can include a wound dressing 330 configured to be positioned proximate to a wound. Multiple optical fibers can be positioned at least partly in the wound dressing 330. An emitter 320 can emit electromagnetic radiation into an emitting optical fiber 310 such that the electromagnetic radiation travels through the emitting optical fiber 310. A detector 350 can generate a signal responsive to reflected electromagnetic radiation captured by detecting optical fiber 340 and that contacts the detector 350. Optical fibers can run outside of the wound dressing 330 and then pierce into the wound dressing 330 (e.g., through-plane) to transmit or receive electromagnetic radiation at locations as illustrated by FIG. 3. The optical fibers described herein can be constructed of polymeric material, glass, or quartz.

An emitting optical fiber 310 can be positioned substantially outside the wound dressing 330. A first end of the emitting optical fiber 310 can be connected to an emitter 320, such as a LED or any other optoelectronic source including, OLED, photodiodes, laser diodes etc. The emitter 320 can be a single source or a multisource emitter with multiple emitters or multiple optical fibers. A second end of the emitting optical fiber 310 can penetrate through the wound dressing 330 such that electromagnetic radiation can travel from the emitter 320 through the emitting optical fiber 310 and onto the wound.

The wound treatment apparatus 300 can further include a detecting optical fiber 340. A first end of the detecting optical fiber 340 can be attached to a detector 350, such as a sensor capable of detecting electromagnetic radiation. The detector 350 can include of a wide variety of sensors, such as photo-resistors, or Light Dependent Resistors (LDR), that changes resistance according to light intensity, photodiodes, charge coupled devices (CCD) or other light sensors. It is also possible to integrate miniaturized sensing elements on the micro-scale to nano-scale order at or within the tip of the fiber, though this may negate the advantage of non-localized electronics discussed in this disclosure. The detector 350 can include a single receiving sensor or multiple receiving sensors. A second end of the detecting optical fiber 340 can penetrate through the wound dressing 330 such that the electromagnetic radiation that exited the emitting optical fiber 310 and is reflected off of the wound can enter the detecting optical fiber 340 where it is transmitted to the detector 350. It should be noted that a single optical fiber can be used to both or either emit and detect electromagnetic radiation.

As illustrated in FIG. 3, the emitter 320 and the detector 350 can advantageously, in certain implementations, be positioned away from the wound dressing. Thus, sensitive electronics can be kept at a safe distance while still being able to function appropriately via the optical fibers. Electronic and conductive elements can be kept away from the vicinity of the wound and improve electrical isolation for the patient.

The detector 350 can detect the reflected electromagnetic radiation and generate a signal responsive to the reflected electromagnetic radiation, which can then be processed by the optical processor 295. The reflected electromagnetic radiation can include a portion of the emitted electromagnetic radiation that was reflected off of the wound.

The signal output from the detector 350 can be used to determine a measurement value indicative of wound characteristics (e.g., temperature, pressure, or exudate features). Direct optical measurement/observation of the wound or local tissue may be possible. Temperature identification can be detected by color changing thermochromic material. The wound treatment apparatus 300 can detect the temperature based on the detected electromagnetic radiation using optical thermometers. The absence of negative pressure can be identified based on the presence or absence of total internal reflection within an optical fiber. Some implementations can implement multiplexing techniques where the light source is polarized for sectionable area interrogation. For instance, half of a wound or wound dressing can be investigated via polarized light in one direction opposite to the other side, such that two direct streams of light are measured. This method may be extended to multiple color streams via color filtration in some implementations.

Optical measurements can be taken of the pH levels by color changing pH sensitive materials such as dyes or gels. Such pH sensitive materials may be encapsulated within the dressing.

Moreover, reduced pressure can be supplied to the wound dressing 330 based on the measurement values indicative of the wound characteristics. Additionally, the notifications can be provided to user equipment (for instance, by activation of an indicator, such as to provide notice of detection of an excess of exudate) based on the measurement values indicative of the wound characteristics. Updates can be provided on the status of a wound, for instance, color, temperature, or other characteristics that can be used to gain understanding of the healing process based on the measurement values indicative of the wound characteristics.

Figure 4:
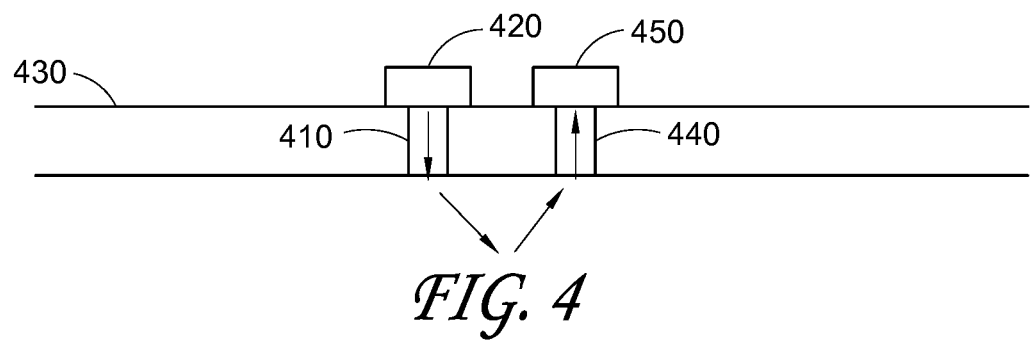
FIG. 4 illustrates an example path of electromagnetic radiation incident through multiple optical fibers.

FIG. 4 illustrates a through-plane example path for electromagnetic radiation through a wound dressing 430, which can be similar to or the same as the wound dressing 330. An emitter 420 and a detector 450 can be positioned on or within a non-sterile portion of the wound dressing 430. As illustrated, the emitter 420 can transmit electromagnetic radiation, via an emitting optical fiber 410, through a plane created by the wound dressing 430 (e.g., orthogonal to a direction that the wound dressing 430 extends over a wound). Similarly, the detector 450 can positioned on or within a non-sterile portion of the wound dressing 430 such that the detector 450 can receive, via a detecting optical fiber 440, reflected electromagnetic radiation along a path that is perpendicular to the plane created by the wound dressing 430.

Figure 5:
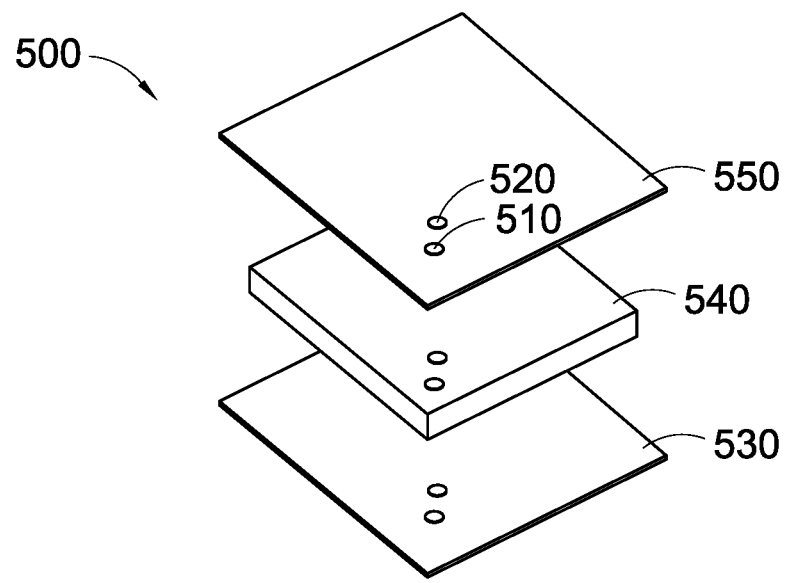
FIG. 5 illustrates an example tri-laminate wound dressing with positions for optical fibers.

FIG. 5 illustrates a wound dressing 500 that has a tri-laminate configuration with positions for optical fibers. The wound dressing 500 can include an emitting position 510 for the passage of an emitting optical fiber into the wound dressing 500. The wound dressing 500 can include a detecting position 520 configured to allow passage of a detecting optical fiber.

Both an emitting optical fiber and a detecting optical fiber can utilize the same opening in the wound dressing 500 in some implementations. Additionally, it will be understood that although one emitting position 510 and one detecting position 520 are illustrated, there may be multiple positions to match multiple optical fibers. As discussed in greater detail herein, the detecting position 520 and the emitting position 510 can be located relative to one another so as to maximize an amount electromagnetic radiation being reflected into one or more detecting optical fibers.

The wound dressing 500 can include a wound filler and a wound cover, such that the optical fibers extend through the wound filler and the wound cover. As illustrated in FIG. 5, a tri-laminate dressing can consist of a perforated wound contact layer 530, a polyurethane absorbent core 540, and a breathable bacterial bather top film 550. A sensor layer can be incorporated in multiple locations in this construct; (e.g., above the top film 550, replacing the top film 550, between the top film 550 and polyurethane absorbent core 540, between the polyurethane absorbent core 540 and the wound contact layer 530, and replacing the wound contact layer 530). Additionally, a bi-laminate dressing can be formed, wherein a cushioning or protective layer may be placed between the sensor sheet and the wound. This can allow even topography to avoid pressure points within the sensory architecture. The sensor layer can be at least partly manufactured from conductive printed materials to maintain a low-profile architecture.

Figure 6:
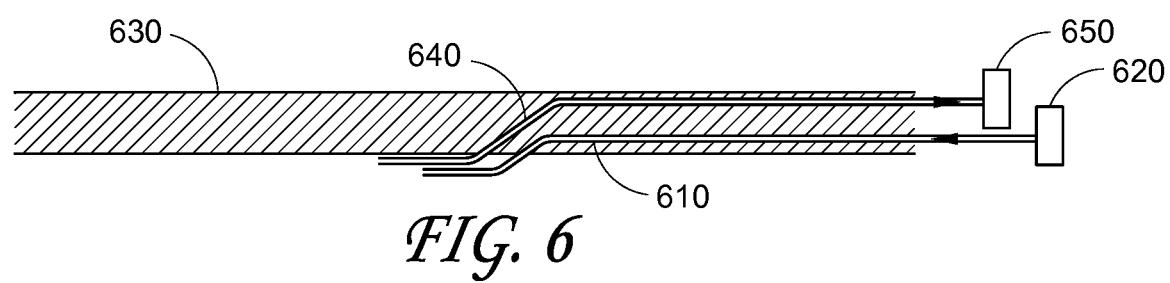
FIG. 6 illustrates example optical fibers in the plane of a wound dressing.

FIG. 6 illustrates an example in-plane path for optical fibers through a wound dressing 630, which can be similar to or the same as the wound dressing 330. As illustrated, an emitting optical fiber 610 and a detecting optical fiber 640 can run within the wound dressing 630 itself and extend in a direction in which the wound dressing 630 extends over a wound. The emitting optical fiber 610 and the detecting optical fiber 640 can then exit the wound dressing 630 to emit and detect electromagnetic radiation onto and from the wound bed. After exiting the wound dressing 630, the emitting optical fiber 610 and the detecting optical fiber 640 can continue to run between the wound dressing 630 and the wound, parallel to the wound dressing 630. An emitter 620 can be used to emit electromagnetic radiation, and a detector 650 can be used to detect electromagnetic radiation.

Figure 7A:
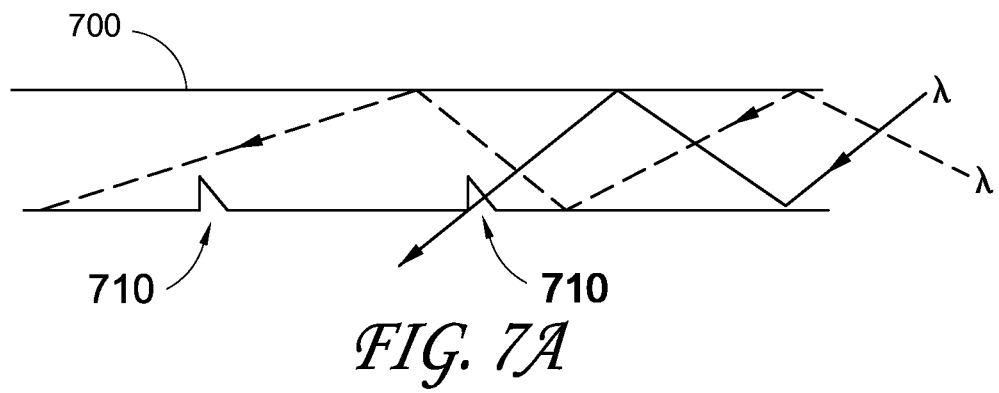
FIGS. 7A, 7B, and 7C illustrate examples of notched or slotted optical fibers with multiple exit locations for use with a wound dressing.
Figure 7B:
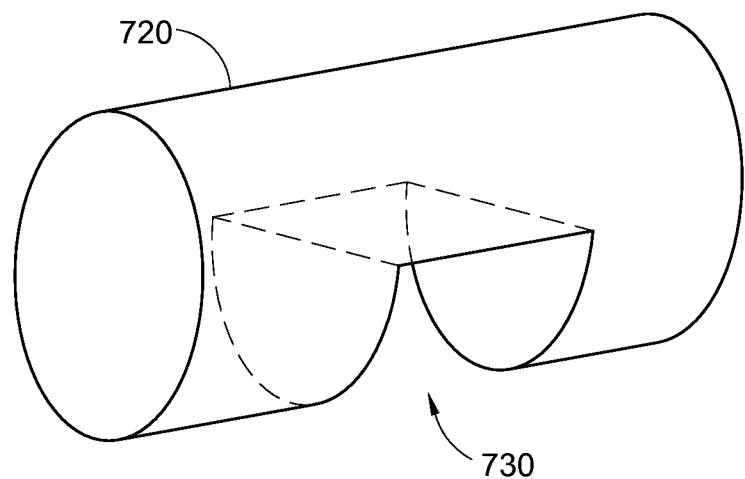
Figure 7C:
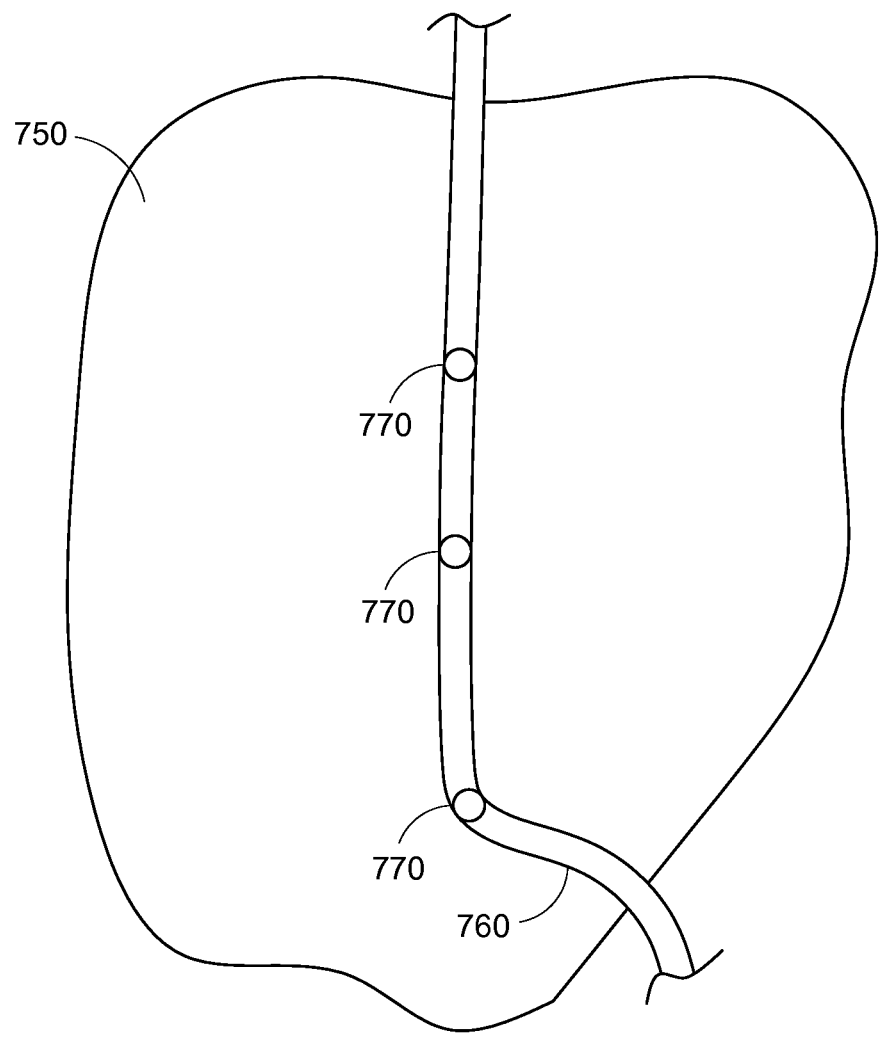

FIGS. 7A-7C illustrate examples of notched or slotted optical fibers that can integrated with a wound dressing, such as the wound dressing 330, or used in combination with the wound dressing. For instance, FIG. 7A illustrates the an optical fiber 700 with multiple slots 710 (or notches) located along a length of the optical fiber 700 positioned parallel to a wound. The slots 710 can allow electromagnetic radiation to escape or enter the optical fiber 700 at slot locations, such as along a wound bed. In such a manner, electromagnetic radiation can exit or enter the optical fiber 700 at a number of locations rather than just at an end of the optical fiber 700. Moreover, the slots 710 can be positioned so that particular slots emit electromagnetic radiation of certain wavelength or wavelengths but not at another wavelength or wavelengths.

The optical fiber 700 can run partly or completely within or substantially parallel to a wound dressing. Electromagnetic radiation can then be emitted or detected by indexed punching of a wound contact layer, such as the wound contact layer 530, to generate optical pathways. The indexed punching can align with the slots 710. The optical fiber 700 can be notched or slotted by physical punch, laser, or other methods. FIG. 7B illustrates another example of a slot 730 (or a notch) in the an optical fiber 720. It should be understood that the above discussion of slots can apply to both the emitting optical fibers for emitting electromagnetic radiation at various points and the detecting optical fibers for detecting electromagnetic radiation at various points.

FIG. 7C illustrates an example where an optical fiber 760 runs parallel to a wound dressing 750. The optical fiber 760 includes three slots 770 where electromagnetic radiation is released from the optical fiber 760 at three locations. In some implementations, the optical fiber 760 may not be notched, but instead includes portions where the material of the optical fiber 760 has an appropriate refractive index to allow the electromagnetic radiation to be directed onto a wound.

Figure 8:
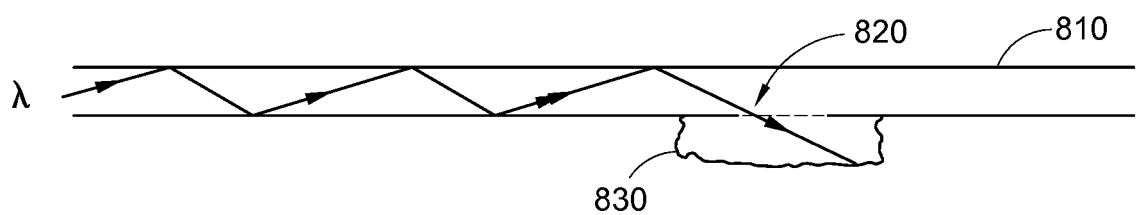
FIG. 8 illustrates an example adhesive contact on an optical fiber that allows electromagnetic radiation to pass to the wound a defined location.

FIG. 8 illustrates an emitting optical fiber 810 with a slot 820. An adhesive contact 830 can be positioned on the emitting optical fiber 810 and allow electromagnetic radiation to travel to a wound a defined locations. The adhesive contact 830 can hold the emitting optical fiber 810 in place to ensure the electromagnetic radiation continues to exit the emitting optical fiber 810 at the proper locations. An adhesive contact can also be used to hold a detecting optical fiber in a fixed location with respect to a wound or a wound dressing.

A wound dressing can be constructed to allow contact of an optical fiber with a construction adhesive above a transparent wound contact layer, allowing electromagnetic radiation to be transmitted to the wound, whilst encapsulating the optical fiber within the wound dressing.

Figure 9:
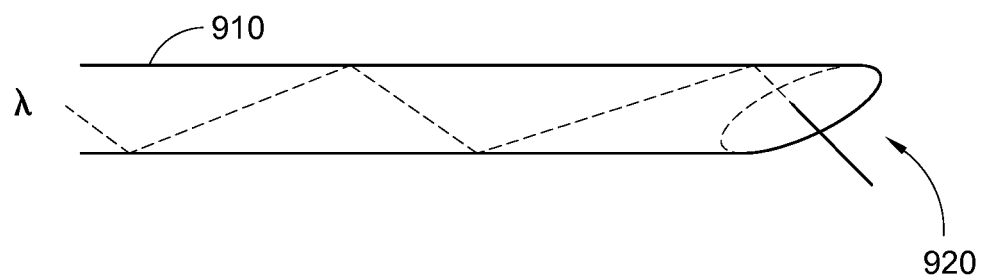
FIG. 9 illustrates an example truncated optical fiber that allows electromagnetic radiation to exit at angles.
Figure 10A:
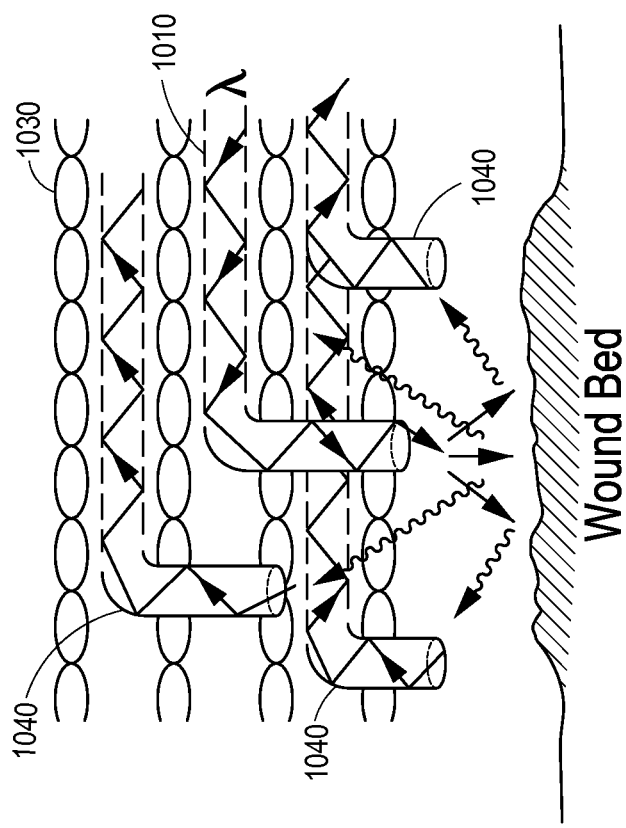
FIGS. 10A, 10B, 10C, and 10D illustrate various example configurations of optical fibers for use with wound dressings.

FIG. 9 illustrates an optical fiber 910 with a truncated end 920. The truncated end 920 can be truncated at a particular angle and thereby cause electromagnetic radiation to exit or enter the optical fiber 910 at various angles. For instance, the truncated end 920 can allow electromagnetic radiation exiting the optical fiber 910 to be incident on a wound or entering the optical fiber 910 to enter without having an end of the optical fiber 910 face toward the wound, such as is shown in FIG. 10A. Further, the truncated end 920 can allow electromagnetic radiation exiting the optical fiber 910 to scatter. When the optical fiber 910 serves as a detecting optical fiber, an end of optical fiber 910 can be truncated at an angle so that reflected electromagnetic radiation may, for instance, more likely to enter at the end.

Figure 10D:
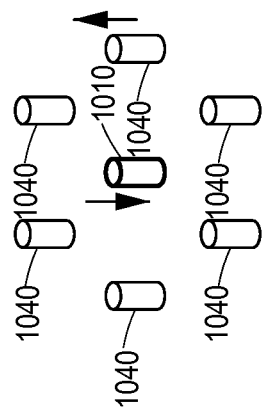
Figure 10C:
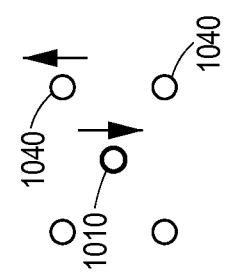
Figure 10B:
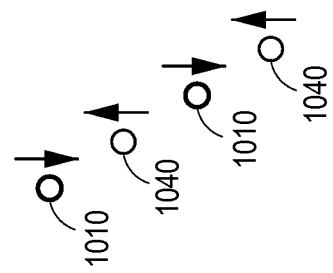

FIGS. 10A-10D illustrate various example configurations of optical fibers. The optical fibers can be angled at the ends in order to emit or detect electromagnetic radiation at predetermined locations. For example, the optical fibers can be angled approximately 90 degrees such that the optical fibers transition from substantially parallel to a wound dressing 1030 to substantially perpendicular to the wound dressing 1030. There may be a single emitting optical fiber 1010 surrounded by multiple detecting optical fibers 1040. As illustrated in FIGS. 10B-10D, there are a number of possible configurations and layouts for the optical fibers. For instance, FIG. 10B illustrates a configuration with alternating emitting optical fibers 1010 and detecting optical fibers 1040. FIG. 10C illustrates a configuration in which a single emitting optical fiber 1010 in the center of four detecting optical fibers 1040, and the detecting optical fibers 1040 form a square pattern around the emitting optical fiber 1010. Likewise, FIG. 10D illustrates a configuration in which a single emitting optical fiber 1010 is surrounded by detecting optical fibers 1040, and the detecting optical fibers 1040 form a hexagon pattern around the emitting optical fiber 1010. The various configurations that can be selected for particular wound sizes, wound shapes, or wound dressings, for instance, to maximize an amount of reflected electromagnetic radiation that the detecting optical fibers 1040 detect.

Figure 11:
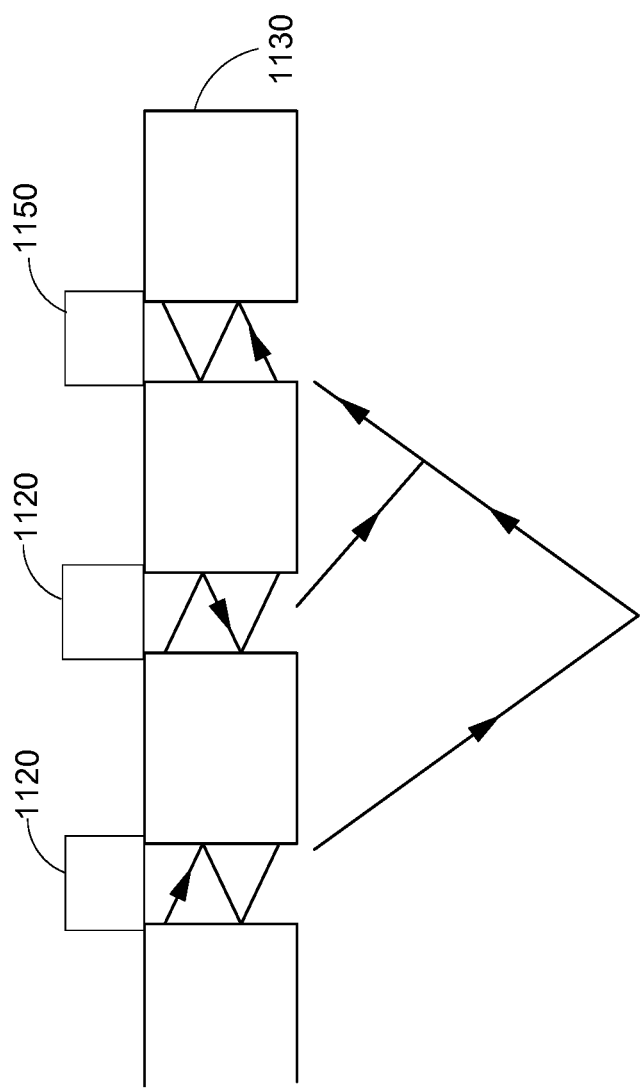
FIG. 11 illustrates an example configuration of multiple emitters for use with wound dressings.

FIG. 11 illustrates a wound dressing 1130 with multiple emitting optical fibers and a detecting optical fiber. The multiple emitting optical fibers can be coupled to one or more emitters 1120. The detecting optical fiber can be coupled to a detector 1150 that detects electromagnetic radiation passing through the detecting optical fiber. As can be seen from FIG. 11, the illustrated configuration may be used to transmit and reflect electromagnetic radiation at different depths in a wound area to determine wound characteristics at the different depths.

Figure 12:
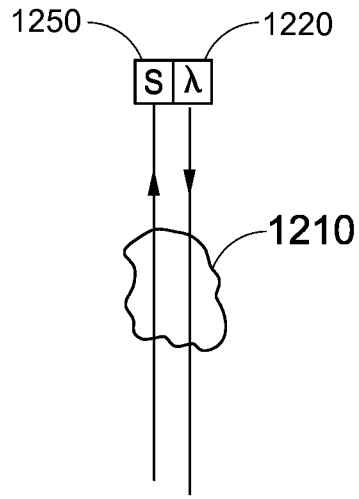
FIG. 12 illustrates an example optical fiber usable to detect liquid, such as wound exudate.

FIG. 12 illustrates an emitter 1220 and a detector 1250 being used to detect liquid 1210, such as wound exudate. As is discussed herein, a wound dressing can be constructed to allow emitting and detecting optical fibers to pass and detect electromagnetic radiation under the wound dressing. The electromagnetic radiation can be used, for instance, to detect wound exudate that may be accumulating under or within the wound dressing. The optical fibers can, for example, be within the wound dressing and detect when wound exudate enters the wound dressing from a variation in the electromagnetic radiation (for instance, a change in light intensity) detected by the detector 1250.

Figure 13:
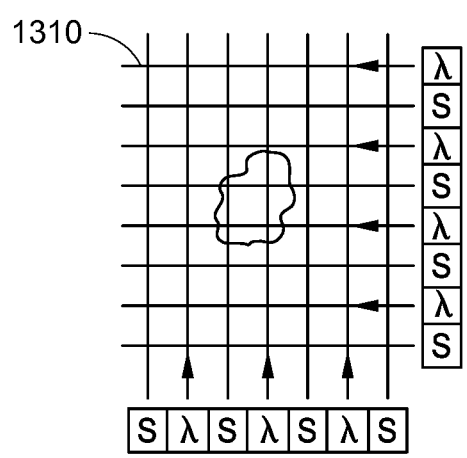
FIG. 13 illustrates example optical fibers positioned in a grid configuration.

FIG. 13 illustrates optical fibers 1310 in a grid configuration, with emitting optical figures being illuminated by emitters 1, and detecting optical fibers detecting with detectors S. The optical fibers 1310 can be arranged in a grid pattern or a zig zag to locate a position or extent of wound exudate across a wound dressing. Such a configuration can be used to determine how saturated the wound dressing may be and thus to indicate an appropriate time for changing the wound dressing.

Other Variations and Terminology

One or more electronic components can be positioned on or around a wound dressing that incorporates one or more optical fibers. For example, the one or more electronic components can be on the side of a wound contact layer opposite the side that faces the wound.

Although certain examples herein are described in the context of wound dressings, the features disclosed herein can apply to other objects or materials. For example, optical fibers can pass through fabrics, garments, shielding, or other barriers to permit electromagnetic radiation to enter or exit the optical fibers for enabling monitoring through the fabrics, garments, shielding, or other barriers.

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value. Moreover, although blocks of the various processes may be described in terms of determining whether a value meets or does not meet a particular threshold, the blocks can be similarly understood, for example, in terms of a value (i) being below or above a threshold or (ii) satisfying or not satisfying a threshold.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as controllers, processors, ASICs, FPGAs, and the like, can include logic circuitry. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A wound treatment apparatus comprising:
 a wound dressing comprising a wound cover and a wound filler configured to absorb wound exudate, the wound dressing being configured to be positioned proximate to a wound;
 a plurality of optical fibers positioned at least partly in the wound dressing so that first ends of the plurality of optical fibers are positioned on an opposite side of the wound cover from second ends of the plurality of optical fibers, the plurality of optical fibers comprising a first optical fiber and a second optical fiber, and a set of optical fibers of the plurality of optical fibers arranged in a grid pattern to detect a saturation level of the wound dressing by the wound exudate;
 a mechanochromic material configured to indicate a pressure at the wound, the mechanochromic material being positioned on the same side of the wound cover as the second ends of the plurality of optical fibers;
 an emitter configured to emit an electromagnetic radiation into the first end of the first optical fiber, the first optical fiber being configured to pass the electromagnetic radiation entering the first end of the first optical fiber to the mechanochromic material, the second optical fiber being configured to gather and pass an electromagnetic radiation that interacted with the mechanochromic material to the first end of the second optical fiber;
 a detector configured to generate a signal responsive to an electromagnetic radiation exiting the first end of the second optical fiber and contacting the detector, the signal reflecting changes in the mechanochromic material; and a processor configured to:
- determine a measurement value from the signal, the measurement value being indicative of the pressure at the wound;
- detect that the measurement value indicates loss of negative pressure at the wound;
- in response to detecting that the measurement value indicates loss of negative pressure at the wound, activate a pressure source to provide negative pressure to the wound;
- determine that the saturation level of the wound dressing satisfies a threshold; and
- in response to determining that the saturation level of the wound dressing satisfies a threshold, provide an indication that the wound dressing should be replaced.

2. The wound treatment apparatus of claim 1, wherein the emitter is positioned proximate to the first end of the first optical fiber.

3. The wound treatment apparatus of claim 1, wherein the first optical fiber comprises a notch or a slit from which the electromagnetic radiation entering the first end of the first optical fiber exits the first optical fiber.

4. The wound treatment apparatus of claim 1, wherein the electromagnetic radiation entering the first end of the first optical fiber has a wavelength between 300 nm and 2400 nm.

5. The wound treatment apparatus of claim 1, wherein the first end of the first optical fiber is truncated at an angle so that an electromagnetic radiation exiting the first end of the first optical fiber scatters.

6. The wound treatment apparatus of claim 1, wherein the first optical fiber and the second optical fiber extend through the wound filler and the wound cover.

7. The wound treatment apparatus of claim 1, wherein the emitter and the detector are positioned within a non-sterile portion of the wound dressing, and wherein the mechanochromic material is positioned within a sterile portion of the wound dressing.

8. The wound treatment apparatus of claim 1, wherein the plurality of optical fibers comprises a third optical fiber that is configured to pass a different wavelength of electromagnetic radiation than the first optical fiber.

9. The wound treatment apparatus of claim 1, wherein the first optical fiber and the second optical fiber extend parallel to a direction in which the wound dressing extends.

10. The wound treatment apparatus of claim 1, wherein the first optical fiber and the second optical fiber extend perpendicular to a direction in which the wound dressing extends.

11. The wound treatment apparatus of claim 1, further comprising a plurality of detectors including the detector, and the plurality of detectors are positioned around the emitter.

12. The wound treatment apparatus of claim 1, wherein the mechanochromic material is attached to the wound filler.

13. The wound treatment apparatus of claim 1, wherein the wound dressing comprises a wound filler, and the mechanochromic material is positioned between the wound filler and the wound.

14. The wound treatment apparatus of claim 1, wherein the mechanochromic material is positioned proximate to the second end of the first optical fiber and the second end of the second optical fiber.

15. The wound treatment apparatus of claim 1, wherein the mechanochromic material is subject to the same pressure as the wound during application of negative pressure to the wound by the pressure source.

16. A wound treatment apparatus comprising:
- a wound dressing comprising a wound cover and a wound filler configured to absorb wound exudate, the wound dressing being configured to be positioned proximate to a wound;
- a plurality of optical fibers positioned at least partly in the wound dressing, the plurality of optical fibers being arranged in a grid pattern to detect a saturation level of the wound dressing by the wound exudate;
- at least one emitter configured to emit an electromagnetic radiation into a first set of the plurality of optical fibers configured to pass the electromagnetic radiation toward the wound;
- at least one detector configured to generate a signal responsive to an electromagnetic radiation exiting the first set of the plurality of optical fibers, interacting with the wound filler or the wound, and being gathered by a second set of the plurality of optical fibers, the signal indicating the saturation level of the wound dressing; and
- a processor configured to:
  - using the signal, determine that the saturation level of the wound dressing satisfies a threshold; and
  - in response to determining that the saturation level of the wound dressing satisfies a threshold, provide an indication that the wound dressing should be replaced.

17. The wound treatment apparatus of claim 16, further comprising a pressure source configured to provide negative pressure to the wound.

18. The wound treatment apparatus of claim 17, further comprising another plurality of optical fibers configured to monitor a pressure at the wound, wherein the processor is configured to operate the pressure source based on the pressure at the wound.

19. The wound treatment apparatus of claim 16, wherein the at least one emitter comprises a plurality of emitters and the at least one detector comprises a plurality of detectors, and wherein the signal further indicates a position of the wound exudate across the wound dressing.

20. A method comprising:
- collecting exudate with a wound dressing positioned over a wound, the wound dressing comprising a wound cover and a wound filler configured to absorb the exudate;
- emitting electromagnetic radiation into a first optical fiber of a plurality of optical fibers, the plurality of optical fibers being positioned at least partly in the wound dressing so that first ends of the plurality of optical fibers are positioned on an opposite side of the wound cover from second ends of the plurality of optical fibers, a set of optical fibers of the plurality of optical fibers arranged in a grid pattern to detect a saturation level of the wound dressing by the exudate;
- passing the electromagnetic radiation entering the first end of the first optical fiber to a mechanochromic material, the mechanochromic material indicating a pressure at the wound and being positioned on the same side of the wound cover as the second ends of the plurality of optical fibers;
- gathering and passing an electromagnetic radiation that interacted with the mechanochromic material to the first end of the second optical fiber;

generating a signal responsive to an electromagnetic radiation exiting the first end of the second optical fiber, the signal reflecting changes in the mechanochromic material;

determining from the signal a measurement value indicative of the pressure at the wound;

detecting that the measurement value indicates loss of negative pressure at the wound;

in response to detecting that the measurement value indicates loss of negative pressure at the wound, providing negative pressure to the wound;

determining that the saturation level of the wound dressing satisfies a threshold; and in response to determining that the saturation level of the wound dressing satisfies a threshold, providing an indication that the wound dressing should be replaced.

* * * * *